US008298512B2

(12) United States Patent
Brown

(10) Patent No.: US 8,298,512 B2
(45) Date of Patent: *Oct. 30, 2012

(54) METHODS OF DETERMINING β$_{-III}$ TUBULIN EXPRESSION

(75) Inventor: Milton L. Brown, Laurel, MD (US)

(73) Assignee: University of Virginia Patent Foundation, Charlottesville, VA (US)

(*) Notice: Subject to any disclaimer, the term of this patent is extended or adjusted under 35 U.S.C. 154(b) by 1229 days.

This patent is subject to a terminal disclaimer.

(21) Appl. No.: 11/613,663

(22) Filed: Dec. 20, 2006

(65) Prior Publication Data

US 2007/0134161 A1    Jun. 14, 2007

Related U.S. Application Data

(63) Continuation-in-part of application No. 11/628,209, filed as application No. PCT/US2005/019244 on Jun. 1, 2005.

(60) Provisional application No. 60/575,927, filed on Jun. 1, 2004.

(51) Int. Cl.
    A61B 5/00       (2006.01)
    A61B 8/00       (2006.01)
    A61B 10/00      (2006.01)
    A61K 49/00      (2006.01)

(52) U.S. Cl. .......................................... 424/9.1; 424/9.6
(58) Field of Classification Search .................... 424/9.6
    See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 4,587,538 A | 5/1986 | Shanton et al. | |
| 5,401,752 A | 3/1995 | Tokunaga et al. | |
| 5,480,833 A | 1/1996 | Kikkawa et al. | |
| 5,480,883 A | 1/1996 | Spada et al. | |
| 6,187,923 B1 | 2/2001 | Dener et al. | |
| 6,716,614 B1 * | 4/2004 | Donoho et al. | 435/219 |
| 8,178,545 B2 | 5/2012 | Brown | |
| 2002/0137068 A1 | 9/2002 | Haugland et al. | |
| 2004/0122030 A1 * | 6/2004 | Brown | 514/266.3 |
| 2005/0130897 A1 * | 6/2005 | Ma | 514/12 |
| 2005/0214807 A1 * | 9/2005 | Johnson et al. | 435/6 |
| 2006/0148830 A1 | 7/2006 | Terakado et al. | |
| 2007/0244098 A1 | 10/2007 | Brown | |

FOREIGN PATENT DOCUMENTS

| | | |
|---|---|---|
| AU | 2005249527 B2 | 11/2011 |
| EP | 0 145 225 A2 | 6/1985 |
| EP | 0145225 A2 | 6/1985 |
| EP | 0 495 610 A1 | 7/1992 |
| EP | 0495610 A1 | 7/1992 |
| JP | 62-258368 | 11/1987 |
| JP | 62258368 A | 11/1987 |
| WO | WO 98/23620 | 6/1998 |
| WO | WO-9823620 A1 | 6/1998 |
| WO | WO 99/11623 | 3/1999 |
| WO | WO-9911623 A1 | 3/1999 |
| WO | WO 00/27831 | 5/2000 |
| WO | WO-0027831 A1 | 5/2000 |
| WO | WO 02/28841 | 4/2002 |
| WO | WO-0228841 A2 | 4/2002 |
| WO | WO 02/086078 A3 | 10/2002 |
| WO | WO-02086078 A2 | 10/2002 |
| WO | WO-02086078 A3 | 10/2002 |
| WO | WO 2004/311118 A1 | 4/2004 |
| WO | WO-2004031118 A1 | 4/2004 |
| WO | WO-2005117876 A1 | 12/2005 |

OTHER PUBLICATIONS

Hamel et al. (Biochem. Pharm. 1996, 51, 53-59).*
Xu et al. (Drug Development Research 2002, 55, 91-96).*
Silence et al. (Biochem. 1992, 31, 11133-11137).*
Wikipedia (Keratitis).*
Fluorescein Wikipedia document.*
Wikipedia (Keratitis) 2010.*
Fluorescein Wikipedia document (2011).*
"U.S. Appl. No. 11/613,663, Office Action Response Filed Apr. 3, 2011", 2 pgs.
"U.S. Appl. No. 11/628,209, Restriction Requirement mailed Jul. 1, 2011", 10 pgs.
"Australian Application Serial No. 2005249527, Response filed Jun. 29, 2011 to Examiner Report mailed Dec. 9, 2009", 29 pgs.
"Japanese Application Serial No. 2007-515530, Office Action mailed Jun. 7, 2011", 10 pgs.
Carey, F. A, et al., "Carbonium ion-silane hydride transfer reactions. II. 2-Phenyl-2-norbornyl cation", J. Org. Chem., 34(1), (1969), 887-892.
Cheon, S. H, et al., "Structure-activity relationship studies of isoquinolinone type anticancer agent", Arch Pharm Res., 24(4), (Aug. 2001), 276-80. Cho, W. J, et al., "Molecular modeling of 3-arylisoquinoline antitumor agents active against A-549. A comparative molecular field analysis study", Bioorg Med Chem.,10(9), (Sep. 2002), 2953-61.
"U.S. Appl. No. 11/628,209 , Response filed Jul. 29, 2011 to Restriction Requirement mailed Jul. 1, 2011", 21 pgs.
"U.S. Appl. No. 11/628,209 , Response filed Oct. 31, 2011 to Non Final Office Action mailed Sep. 20, 2011", 13 pgs.
"U.S. Appl. No. 11/628,209, Non Final Office Action mailed Sep. 20, 2011", 18 pgs.
"European Application Serial No. 05756099.7, Examination Report mailed Oct. 11, 2011", 7 pgs.
Hamel, Ernest, et al., "Antitumor 2, 3-Dihydro-2-(ARYL)-4(1H)-Quinazolinone Derivatives Interactions With Tublin", Biochemical Pharmacology Pergamon, Oxford, GB, vol. 51, No. 1, (Jan. 1, 1996), 53-59.

(Continued)

Primary Examiner — Michael G Hartley
Assistant Examiner — Melissa Perreira
(74) Attorney, Agent, or Firm — Schwegman Lundberg & Woessner, P.A.

(57) ABSTRACT

Provided are methods of determining the quantity and location of β$_{III}$-tubulin expression in a subject, which may be used to determine the location and/or extent of excessive or uncontrolled growth of cells such as tumors. Such methods may include administering at least one compound to a patient and determining the quantity and location of β$_{III}$ tubulin expression within the patient by visualizing the compound within the patient. Visualization of the compound may be indicative of the binding of the compound to cells that are actively expressing β$_{III}$ tubulin.

15 Claims, 8 Drawing Sheets

OTHER PUBLICATIONS

Kamb, Alexander, "Wnat's wrong with our cancer models", Nature Reviews Drug Discovery, 2, (2005), 161-165.

Moore, James A, et al., "Reactions of anthranilamide and o-aminoacetophenone with benzil and benzoin", J. Org. Chem., 34(4), (1969), 887-892.

Poupaert, Jacques H, "Drug Design: Basic Principles and Applications", In 2 Encyclopedia of Pharmaceutical Technology, (James Swarbrick ed., 3rd ed., ), (2007), 9 pgs.

Sharpless, Norman E, et al., "The mighty mouse: genetically engineered mouse models in cancer drug development", Nature Reviews Drug Discovery 5, (2006), 14 pgs.

Smith, Nicola F, et al., "The application of cassette dosing for pharmacokinetic screening in small-molecule cancer drug discovery", Molecular Cancer Therapeutics, 6,, (2007), 428-440.

Veljkovic, V., et al., "Application of the EIIP/ISM Bioinformatics Concept in Development of New Drugs", Current Medicinal Chemistry, 14,, (2007), 441-453.

Zon, Leonard I, et al., "In Vivo Drug Discovery in the Zebrafish", Nature Reviews Drug Discovery, 4, (Jan. 2005), 35-44.

"U.S. Appl. No. 11/628,209, Notice of Allowability mailed Jan. 26, 2012", 3 pgs.

"U.S. Appl. No. 11/628,209, Notice of Allowance mailed Dec. 27, 2011", 7pgs.

"U.S. Appl. No. 11/628,209, Response filed Feb. 6, 2012 to Notice of Allowance mailed Dec. 27, 2011", 3 pgs.

"U.S. Appl. No. 11/628,209, Response to Rule 312 Communication mailed Feb. 10, 2012", 2 pgs.

"Canadian Application Serial No. 2,568,622, Office Action mailed Feb. 23, 2012", 3 pgs.

"European Application Serial No. 05756099.7, Office Action Response filed Jan. 27, 2012", 26 pgs.

"Israeli Application Serial No. 179714, Office Action mailed Dec. 24, 2011", 2 pgs.

"Japanese Application Serial No. 2007-515530, Office Action Response filed Oct. 5, 2011", 13 pgs.

"U.S. Appl. No. 13/366,726, Preliminary Amendment mailed Apr. 24, 2012", 13 pgs.

"Israeli Application Serial No. 179714, Response filed Mar. 25, 2012 to Office Action mailed Oct. 24, 2011", 2 pgs.

"Korean Application Serial No. 10-2006-7027847, Office Action mailed Mar. 2, 2012", W/ English Translation, 19 pgs.

Cooper, C. R, et al., "A Novel Compound Inhibits the Growth of Human Bone Marrow Endothelial Cells and Bone Metastasizing Prostate Cancer Cells", IV International Conference on Cancer-Induced Bone Diseases, Abstract 53, (Dec. 7, 2003), 43 pgs, vol. 19, issue 9, Sep. 2004, p. 1559-1600.

Hamel, Ernest, et al., "Antitumor 2, 3-Dihyrdo-2-(aryl)-4(1H)-quinazolinone Derviatives", Biochemical Pharmacology, vol. 51, Interaction With Tubulin, (1996), 8 pgs, vol. 51, Issue 1, Jan. 1996, pp. 53-59.

European Search Report, Serial No. EP 05756099.7, mailed Nov. 15, 2007.

PCT Search Report, Serial No. PCT/US2005/19244, filed Jun. 1, 2005, mailed Oct. 14, 2006.

Chemical Abstracts—Registry Record [452326-39-5].

Altschul, et al., Basic Local Alignment Search Tool, J. Mol. Biol., 1990, vol. 215, pp. 403-410.

Altschul et al., Gapped BLAST and PSI-BLAST: a new generation of protein database search programs, Nucleic Acids Research., 1997, vol. 25, pp. 3389-3402.

Banerjee et al., A Monoclonal Antibody against the Type II Isotype of β-Tubulin, J. Biol. Chem. 1988, vol. 263, pp. 3029-3034.

Braguer et al., Differentiation of human colon cancer cells changes the expression of β-tubulin isotypes and MAPs, British Journal of Cancer, 1999, vol. 80, pp. 1162-1168.

Brem et al., Interstitial chemotherapy with drug polymer implants for the treatment of recurrent gliomas, J. Neurosurg., 1991, vol. 74, pp. 441-446.

Brown, et al., Comparative Molecular Field Analysis of Colchicine Inhibition and Tubulin Polymerization for Combretastatins Binding to the Colchicine Binding Site on β-Tubulin, Bioorganic and Medicinal Chemistry, 2000, vol. 8, pp. 1433-1441.

Griffin et al., Resistance-Modifying Agents. 5.[1] Synthesis and Biological Properties of Quinazolinone Inhibitors of the DNA Repair Enzyme Poly(ADP-ribose) Polymerase (PARP), 1998, J. Med. Chem., vol. 41, pp. 5247-5256.

Hollstein et al., p53 Mutations in Human Cancers, Science, 1991, vol. 253, pp. 49-53.

Holwell et al., Anti-tumor and Anti-vascular Effects of the Novel Tubulin-binding Agent Combretastatin A-1 Phosphate, Anticancer Research., 2002, vol. 22, No. 6C, pp. 3933-3940.

Hour et al., 6-Alkylamino-and 2,3-Dihydro-3'-methoxy-2phenyl-4-quinazolinones and Related Compounds: Their Synthesis, Cytotoxicity, and Inhibition of Tubulin Polymerization, Journal of Medicinal Chemistry, 2000, vol. 43, pp. 4479-4487.

Karlin et al., Methods for assessing the statistical significance of molecular sequence features by using general scoring schemes, Proc. Natl. Acad. Sci. USA, 1990, vol. 87, pp. 2264-2268.

Karlin et al., Applications and statistics for multiple high-scoring segments in molecular sequences, Proc. Natl. Acad. Sci. USA, 1993, vol. 90, pp. 5873-5877.

Jordan, M.A., Mechanism of Action of Antitumor Drugs that Interact with Microtubules and Tubulin, Curr. Med. Chem., 2002, vol. 2, pp. 1-17.

Miller, et al., Redefining the Target : Chemotherapeutics as Antiangiogenics, J. Clin. Oncol., 2001 vol. 19, No. 4, pp. 1195-1206.

Roach et al., Preparation of a Monoclonal Antibody Specific for the Class I Isotype of β-Tubulin, Cell Motility and the Cytoskeleton 1998, vol. 39, pp. 273-285.

Rowinsky, E. K. et al., Antimicrotule Agents, Cancer Principles and Practice of Oncology, 6th edition, 2001,vol. 1, pp. 431-447.

Saclarides et al., Tumor Angiogenesis and Rectal Carcinoma, Diseases of the Colon & Rectum, 1994, vol. 37, pp. 921-926.

Safran, et al., p53 Mutations Do Not Predict Response to Paclitaxel/Radiation for Nonsmall Cell Lung Carcinoma, Cancer, 1996, vol. 78, pp. 1203-1210.

Tinley, et al., Novel 2-Methoxyestradiol Analogues with Antitumor Activity, Cancer Research., 2003, vol. 63, pp. 1538-1549.

Verdier-Pinard et al., Analysis of Tubulin Isotypes and Mutations from Taxol-Resistant Cells by Combined Isoelectrofocusing and Mass Spectrometry, Biochemistry, 2003, vol. 42, pp. 5349-5357.

"U.S. Appl. No. 11/628,209, Preliminary Amendment mailed Dec. 1, 2006", 3 pgs.

"Australian Application Serial No. 2005249527, First Examination Report mailed Dec. 9, 2009", 2 pgs.

"Chemical Abstracts", Registry Record 452326-39-5, 1 pg.

"European Application Serial No. 05756099.7, European Search Report mailed Nov. 15, 2007", 3 pgs.

"International Application Serial No. PCT/US2005/019244, International Preliminary Examination Report mailed Dec. 4, 2006", 6 pgs.

"International Application Serial No. PCT/US2005/019244, International Search Report and Written Opinion mailed Oct. 14, 2005", 10 pgs.

"Israeli Application Serial No. 179714, Non Final Office Action mailed Aug. 3, 2010", 2.

"Singapore Application Serial No. 200608386-9, Search Report mailed Jan. 1, 2009", 9 pgs.

Altschul, S. F., "Basic Local Alignment Search Tool", J. Mol. Biol., 215(3), (1990), 403-410.

Altschul, S. F., "Gapped BLAST and PSI-BLAST: A New Generation of Protein Database Search Programs", Nucleic Acids Research, 25(17), (1997), 3389-3402.

Banerjee, A., et al., "A monoclonal antibody against the type II isotype of beta-tubulin. Preparation of isotypically altered tubulin.", J Biol Chem., 263(6), (Feb. 25, 1988), 3029-34.

Brem, H., et al., "Interstitial chemotherapy with drug polymer implants for the treatment of recurrent gliomas.", J Neurosurg., 74(3), (Mar. 1991), 441-6.

Brown, M. L, et al., "Comparative molecular field analysis of colchicine inhibition and tubulin polymerization for combretastatins binding to the colchicine binding site on beta-tubulin.", Bioorg Med Chem., 8(6), (Jun. 2000), 1433-41.

Carles, G., et al., "Differentiation of human colon cancer cells changes the expression of beta-tubulin isotypes and MAPs.", Br J Cancer., 80(8), (Jun. 1999), 1162-8.

Griffin, R. J, et al., "Resistance-modifying agents. 5. Synthesis and biological properties of quinazolinone inhibitors of the DNA repair enzyme poly(ADP-ribose) polymerase (PARP).", J Med Chem., 41(26), (Dec. 17, 1998), 5247-56.

Hollstein, M., et al., "p53 mutations in human cancers.", Science, 253(5015), (Jul. 5, 1991), 49-53.

Holwell, S. E, et al., "Anti-tumor and anti-vascular effects of the novel tubulin-binding agent combretastatin A-1 phosphate.", Anticancer Res., 22(6C), (Nov.-Dec. 2002), 3933-40.

Hour, M. J, et al., "6-Alkylamino- and 2,3-dihydro-3'-methoxy-2-phenyl-4-quinazolinones and related compounds: their synthesis, cytotoxicity, and inhibition of tubulin polymerization.", J Med Chem., 43(23), (Nov. 16, 2000), 4479-87.

Jordan, M. A, "Mechanism of action of antitumor drugs that interact with microtubules and tubulin.", Curr Med Chem Anticancer Agents, 2(1), (Jan. 2002), 1-17.

Karlin, S., et al., "Applications and statistics for multiple high-scoring segments in molecular sequences.", Proc Natl Acad Sci U S A., 90(12), (Jun. 15, 1993), 5873-7.

Karlin, S., et al., "Methods for assessing the statistical significance of molecular sequence features by using general scoring schemes.", Proc Natl Acad Sci U S A., 87(6), (Mar. 1990), 2264-8.

Miller, K. D, et al., "Redefining the target: chemotherapeutics as antiangiogenics", J Clin Oncol., 19(4), (Feb. 15, 2001), 1195-206.

Roach, M. C, et al., "Preparation of a monoclonal antibody specific for the class I isotype of beta-tubulin: the beta isotypes of tubulin differ in their cellular distributions within human tissues.", Cell Motil Cytoskeleton, 39(4), (1998), 273-85.

Rowinsky, E. K, et al., "Antimicrotule Agents", Cancer Principles and Practice of Oncology, 6th ed., vol. 1, (2001), 431-447.

Saclarides, T. J, et al., "Tumor angiogenesis and rectal carcinoma", Dis Colon Rectum., 37(9), (Sep. 1994), 921-6.

Safran, H., et al., "p53 mutations do not predict response to paclitaxel/radiation for nonsmall cell lung carcinoma.", Cancer, 78(6), (Sep. 15, 1996), 1203-10.

Tinley, T. L, et al., "Novel 2-methoxyestradiol analogues with anti-tumor activity.", Cancer Res., 63(7), (Apr. 1, 2003), 1538-49.

Verdier-Pinard, P., et al., "Analysis of tubulin isotypes and mutations from taxol-resistant cells by combined isoelectrofocusing and mass spectrometry", Biochemistry, 42(18), (May 13, 2003), 5349-57.

* cited by examiner

Control

33 µM SC-2-71

Control 1.65 µM SC-2-71

Fig. 4.

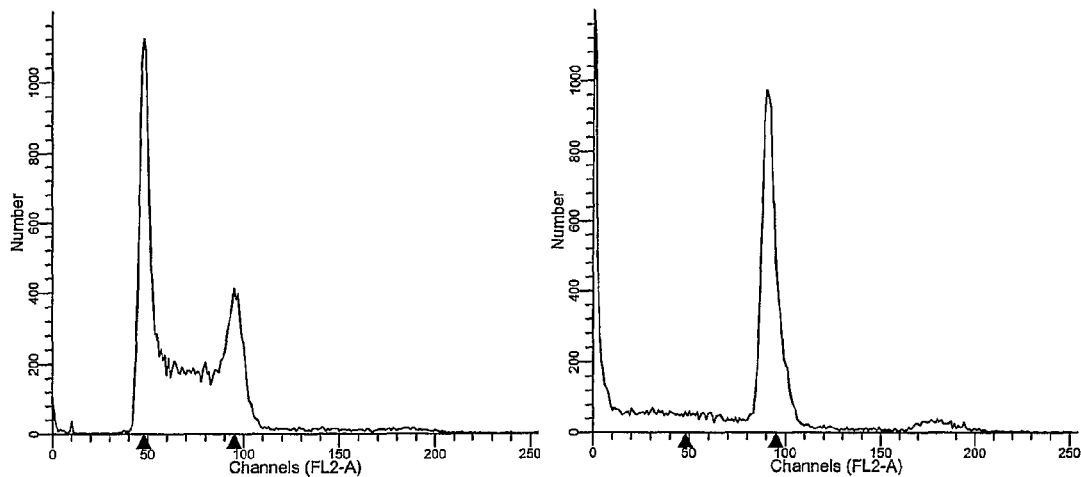

Fig. 5.

```
III      MREIVHIQAGQCGNQIGAKFWEVISDEHGIDPSGNYVGDSDLQLERISVYYNEASSHKYV  60
crystal  MREIVHIQAGQCGNQIGAKFWEVISDEHGIDPTGSYHGDSDLQLERINVYYNEAAGNKYV  60

III      PRAILVDLEPGTMDSVRSGAFGHLFRPDNFIFGQSGAGNNWAKGHYTEGAELVDSVLDVV  120
crystal  PRAILVDLEPGTMDSVRSGPFGQIFRPDNFVFGQSGAGNNWAKGHYTEGAELVDSVLDVV  120

III      RKECENCDCLQGFQLTHSLGGGTGSGMGTLLISKVREEYPDRIMNTFSVVPSPKVSDTVV  180
crystal  RKESESCDCLQGFQLTHSLGGGTGSGMGTLLISKIREEYPDRIMNTFSVVPSPKVSDTVV  180

III      EPYNATLSIHQLVENTDETYCIDNEALYDICFRTLKLATPTYGDLNHLVSATMSGVTTSL  240
crystal  EPYNATLSVHQLVENTDETYCIDNEALYDICFRTLKLTTPTYGDLNHLVSATMSGVTTCL  240

III      FPGQLNADLRKLAVNMVPFPRLHFFMPGFAPLTRRGSQQYRALTVPELTQQMFDAKNMM   300
crystal  RFPGQLNADLRKLAVNMVPFPRLHFFMPGFAPLTSRGSQQYRALTVPELTQQMFDAKNMM  300

III      AACDPRHGRYLTVATVFRGRMSMKEVDEQMLAIQSKNSSYFVEWIPNNVKVAVCDIPPRG  360
crystal  AACDPRHGRYLTVAAVFRGRMSMKEVDEQMLNVQNKNSSYFVEWIPNNVKTAVCDIPPRG  360

III      LKMSSTFIGNSTAIQELFKRISEQFTAMFRRKAFLHWYTGEGMDEMEFTEAESNMNDLVS  420
crystal  LKMSATFIGNSTAIQELFKRISEQFTAMFRRKAFLHWYTGEGMDEMEFTEAESNMNDLVS  420

III      EYQQYQDA--TAEEEGEMYEDDEEESEAQGPK--------  450
crystal  EYQQYQD---------------------------------  427
```

C: SC-2-71 Docked Near the Taxol Binding Site (A) Taxol (blue) co-crystallized in ß-Tubulin
(B) SC-2-71 (red) docked in ß-Tubulin
(C) SC-2-71 forms a hydrogen bond with Tyr36

SC-4-283

The ketone is in the "vicinity" of the sidechains of His28, Arg369, Lys372.

Figure 11
A
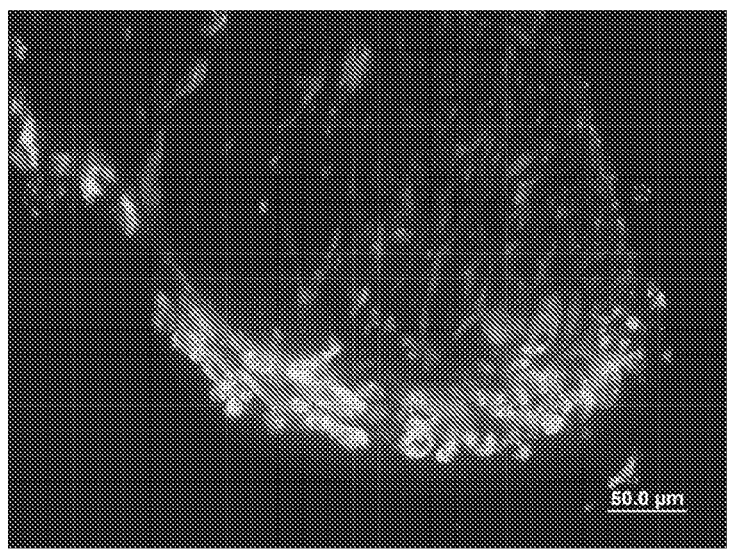
Retinal tissue from AMD patient showing $\beta_{III}$ tubulin (red) and $\beta_{II}$ tubulin (green). Yellow color indicates both isoforms of $\beta$ tubulin within the same cell.
B
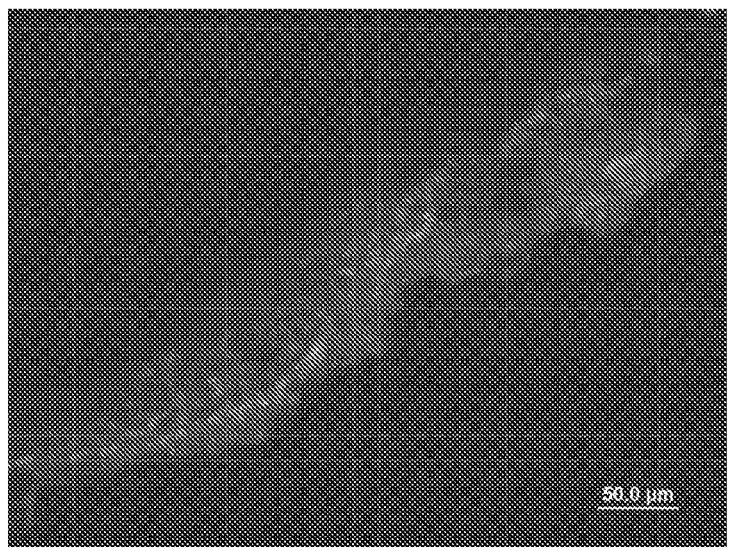
Retinal tissue from Non-AMD patient stained for both isoforms, but only showing $\beta_{II}$ tubulin (green).

METHODS OF DETERMINING $\beta_{-III}$ TUBULIN EXPRESSION

CROSS REFERENCE TO RELATED APPLICATIONS

This application is a continuation-in-part of U.S. application Ser. No. 11/628,209, filed Dec. 1, 2006 as a 371 U.S. National Stage Entry of PCT application US2005/019244, filed Jun. 1, 2005, which, in turn, claims priority, pursuant to 35 U.S.C. §119(e), to U.S. provisional patent application No. 60/575,927, filed Jun. 1, 2004, all of which are incorporated herein by reference.

BACKGROUND

Colorectal cancer is the second most common cause of cancer-related mortality in Europe and North America. This cancer affects nearly 150,000 patients and results in more than 60,000 deaths in the United States per year. Despite significant advances in the management of the colon cancer patient, there has been little change in survival rates over the past 50 years. The primary cause of death relates to the development of distant metastases to organs such as the liver and lungs. Unfortunately, colon cancer still remains one of the most common types of epithelial malignancies in both genders and is essentially incurable when it reaches the most advanced stages.

Surgical resection remains the present standard of care for patients with localized colorectal cancer. Several adjuvant chemotherapy strategies have also emerged and the use of 5-fluorouracil (5-FU) with leucovorin (LV) rescue is now established in stage III colon cancer. Considering the high re-occurrence rates of colon cancer and the side-effects of surgical and chemical therapies, the discovery of novel compounds that block, reverse, delay or prevent the development of invasive large bowel neoplasms would be of major importance.

Adenocarcinoma accounts for 90-95% of all colorectal cancer and the majority of the human cultured cell lines reflect this phenotype. Table 1 summarizes the differences in some available human colon cell lines in relation to age, gender, histology/grade, and source (e.g., ascites vs. primary tumor). These cultured cell lines provide a rich opportunity to evaluate novel compounds for efficacy and to establish their mechanism of action.

TABLE 1

NCI cultured human colon cancer cell lines.

| Cell line[a] | Gender | Patient Age | Histology | Treatment | Source |
|---|---|---|---|---|---|
| COLO 205 | M | 70 | Adenocarcinoma | Y | Ascites |
| HCC-2998 | | | Carcinoma | N | |
| HCT-15 | | | Adenocarcinoma | | |
| HCT-116 | | | Adenocarcinoma/ grade III | | |
| HT29 | F | 44 | Adenocarcinoma | | Primary |
| KM12 | | | Adenocarcinoma | | |
| SW-60 | M | 51 | Adenocarcinoma | N | Metastasis |

[a]Available cell lines from the National Cancer Institute (NCI).

Tubulin, the subunit protein of cellular microtubules, is the target of several effective cancer chemotherapeutic agents currently in clinical use. Tubulin is composed of an α/β heterodimer, and at least six human α-tubulin and seven human β-tubulin isotypes (gene products) are known. Overall, the repertoire of β-tubulin isotypes is believed to play a significant role in development and the building of specialized microtubule-based cellular structures, and general disruption of cellular microtubules is one target for cancer chemotherapy that has proven to be effective.

In many organisms, both α and β tubulin isotypes differ by their tissue distributions. In mammals, the $\beta_I$ and $\beta_{IV}$ isotypes are quite widespread, and $\beta_{II}$ is less so, while $\beta_{III}$ and $\beta_{VI}$ have narrow distributions and $\beta_V$ distribution is unknown. As a tool for localizing the isotypes, the preparation of monoclonal antibodies specific for $\beta_I$, $\beta_{III}$, $\beta_{IV}$ and $\beta_V$ isotypes have been reported (Banerjee et al., J. Biol. Chem. 1988, 263:3029-3034). β-isotypes have been localized in several human tissues including oviduct, skin, colon, and pancreas with striking differences in their tissue distributions. In fact, there is little or no $\beta_{III}$ in these tissues, except for the columnar epithelial cells of the colon (Roach et al., Cell Motility and the Cytoskeleton 1998, 39:4:273-285).

Normal cellular architecture, growth, division, and intracellular transport are dependent on microtubules. Microtubules are versatile and highly dynamic structures that undergo rapid changes in response to cellular signaling from a variety of stimuli. The dynamic instability of microtubules is critical for their normal functions. Drugs that disrupt the dynamic response of microtubules can lead to altered microtubule function, abnormal cellular metabolism, and can ultimately lead to apoptosis.

In cell lines resistant to microtubule-stabilizing drugs that express heterozygous tubulin mutations, the relative amount of mutant tubulin expression is important. In these cell lines, the absence of $\beta_{II}$- and $\beta_{IVa}$-tubulin has been demonstrated, and an increased level of expression of $\beta_{III}$-tubulin in resistant cells has been confirmed (Verdier-Pinard et al., Biochemistry, 42(18):5349-57, 2003), indicating that this tubulin isotype may have a significant role in taxol resistance.

Antimicrotubule agents comprise some of the most widely used and effective cancer chemotherapeutic agents in clinical use (Rowinsky, E. K. and Tolcher, A. W. Antimicrotubule Agents. In: V. T. J. DeVita, S. Hellman, and S. A. Rosenberg (eds.), Cancer Principles and Practice of Oncology, 6th edition, Vol. 1, pp. 431-447. Philadelphia, Pa.: Lippincott Williams and Wilkins, 2001). Prompted by the clinical successes of the vinca alkaloids and taxanes, significant efforts have been focused on identifying new agents that have a similar mechanism of action, but superior properties including the ability to circumvent drug resistance mechanisms, exhibit better solubility and oral availability.

A serious problem associated with the treatment of cancer is the development of drug resistance. Some tumors are intrinsically resistant to chemotherapy and others develop drug resistance during chemotherapy. A significant proportion of tumors are multidrug resistant because of overexpression of membrane proteins that act as drug efflux pumps. Overexpression of the MDR-1 gene product, P-glycoprotein (Pgp), leads to diminished intracellular drug accumulation and to attenuated cytotoxic effects. Clinically, multidrug resistance imparted by the expression of Pgp can limit the utility of many currently available agents including vinblastine, vincristine, taxol and docetaxol. There is a need for new drugs that can circumvent multidrug resistance.

A second major reason for the development of new microtubule-active agents is that microtubule disruptors are in some cases effective against tumors that express abnormal p53. The tumor suppressor gene encoding p53 is the most frequently mutated gene in human cancers. It is estimated that half of all cancers in the United States exhibit altered p53 (Hollstein et al. Science, 253: 49-53, 1991).

In addition, compounds that target cellular microtubules have recently been found to exhibit antiangiogenic activities and this may contribute to their antitumor and anticancer efficacies (Miller, et al.,. J. Clin. Oncol. 19, 1195-1206, 2001). The taxanes, taxol and docetaxel, vinblastine, vincristine, combretastatin (Holwell et al., Anticancer Research. 22(6C):3933-40, 2002) and 2-methoxyestradiol all have anti-angiogenic activity in vivo (Miller, et al., J. Clin. Oncol., 19:1195-1206, 2001).

Angiogenesis is the process by which new blood vessels are formed from pre-existing blood vessels. This process is complex and begins with the degradation of the basement membrane by proteases secreted by activated endothelial cells. Migration and proliferation leads to the formation of solid endothelial cell sprouts into the stromal space. Vascular loops and capillary tubes develop with formation of tight junctions and deposition of new basement membrane. This process is important in normal reproduction, embryonic development, and wound healing. However, improperly regulated angiogenesis has been implicated in many diseases including cancer.

Tumor growth requires the formation of new blood vessels, (i.e., angiogenesis). It is believed that tumor cells initiate and maintain angiogenesis by expressing a network of angiogenic factors, including endothelial growth factors such as vascular endothelial growth factor (VEGF), angiogenic cytokines such as interleukin-8 (IL-8), matrix metalloproteinases (MMP) such as MMP-2 and MMP-9, and adhesion molecules such as integrins and cadherins. Considering the relevance of angiogenesis in tumor progression, anti-angiogenic therapies have emerged as a potentially promising modality of cancer therapy. A variety of purely anti-angiogenic strategies have been developed, including: 1) endogenous angiogenesis inhibitors (e.g., endostatin); 2) blockers of endothelial survival and growth factors/receptors (e.g., VEGF antibody and VEGF receptor tyrosine kinase inhibitor SU6668); and 3) inhibitors of adhesion molecules or MMPs (e.g., antibodies against integrin). Unfortunately, the use of anti-angiogenic agents to treat cancer has proved challenging and purely anti-angiogenic strategies have failed in the clinic. While these agents inhibit tumor angiogenesis in animal studies, complete suppression of angiogenesis or tumor shrinkage in patients has been uncommon.

There is a long felt need in the art for a better method to identify and prepare compounds capable of regulating cancer cells, angiogenesis, endothelial cells, and tumor formation.

SUMMARY OF THE INVENTION

Example embodiments of the present invention are generally directed to a series of compounds that have anti-microtubulin and/or anti-angiogenic activity. Such compounds, and compositions comprising these compounds, can be used to treat neoplastic diseases and other proliferative disorders, diseases, and conditions associated with excessive or uncontrolled growth of cells, such as tumors. The invention encompasses inhibiting or impeding supplying blood to tissues or cells such as cancer, including inhibiting vascular endothelial cells. Example compounds include selective tubulin inhibitors and the use of such inhibitors to selectively regulate the expression and localization of β-tubulin isotypes in tissues as a means of treating various diseases and disorders, including for example, cancers that previously were difficult to treat using chemotherapeutics.

Other example embodiments are generally directed to methods of determining the quantity and location of $\beta_{III}$ tubulin expression in a patient, which may be used to determine the location and/or extent of excessive or uncontrolled growth of cells. Such methods may include for example, administering at least one compound to a patient and determining the quantity and location of $\beta_{III}$ tubulin expression within the patient by visualizing the compound within the patient. Visualization of the compound may be indicative of the binding of the compound to cells that are actively expressing $\beta_{III}$ tubulin.

Example compounds have the general structure of formula I:

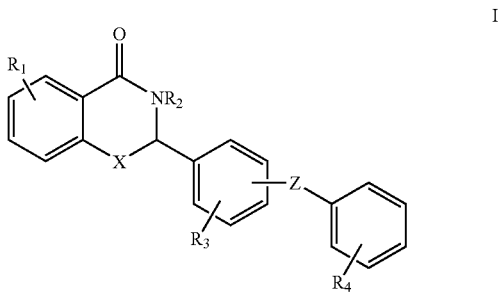

wherein $R_1$, $R_3$ and $R_4$ are independently selected from the group consisting of H, halo, $C_1$-$C_4$ alkyl, $C_2$-$C_4$ alkenyl, $C_2$-$C_4$ alkynyl, $C_1$-$C_4$ alkoxy, and $C_5$-$C_7$ aryl, or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH$(CH_2)_n$)—, $CH_2$, $CHR_5$ and CO; wherein n is 1 or 2;

Z is selected from the group consisting of a bond, O, NH, S, CO, COO, $CH_2O$, $CH_2NH$, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring.

BRIEF DESCRIPTION OF THE DRAWINGS

FIG. 4 Depicts flow cytometric studies of MDA-MB-435 with treated with 3 μM SC-2-71.

FIG. 5 Demonstrates a sequence alignment of $\beta_{III}$ tubulin with the known x-ray structure.

FIG. 11 depicts the fluorescent antibody staining of βII and βIII tubulin in retinal tissue mounts taken from both patients diagnosed with wet acute macular degeneration (wet AMD) (A) and normal patients (B). Staining shows that $β_{III}$ is expressed in tissue taken from a wet AMD patient, whereas normal tissue does not stain positive for $β_{III}$ tubulin.

DETAILED DESCRIPTION OF THE INVENTION

Figure 1:
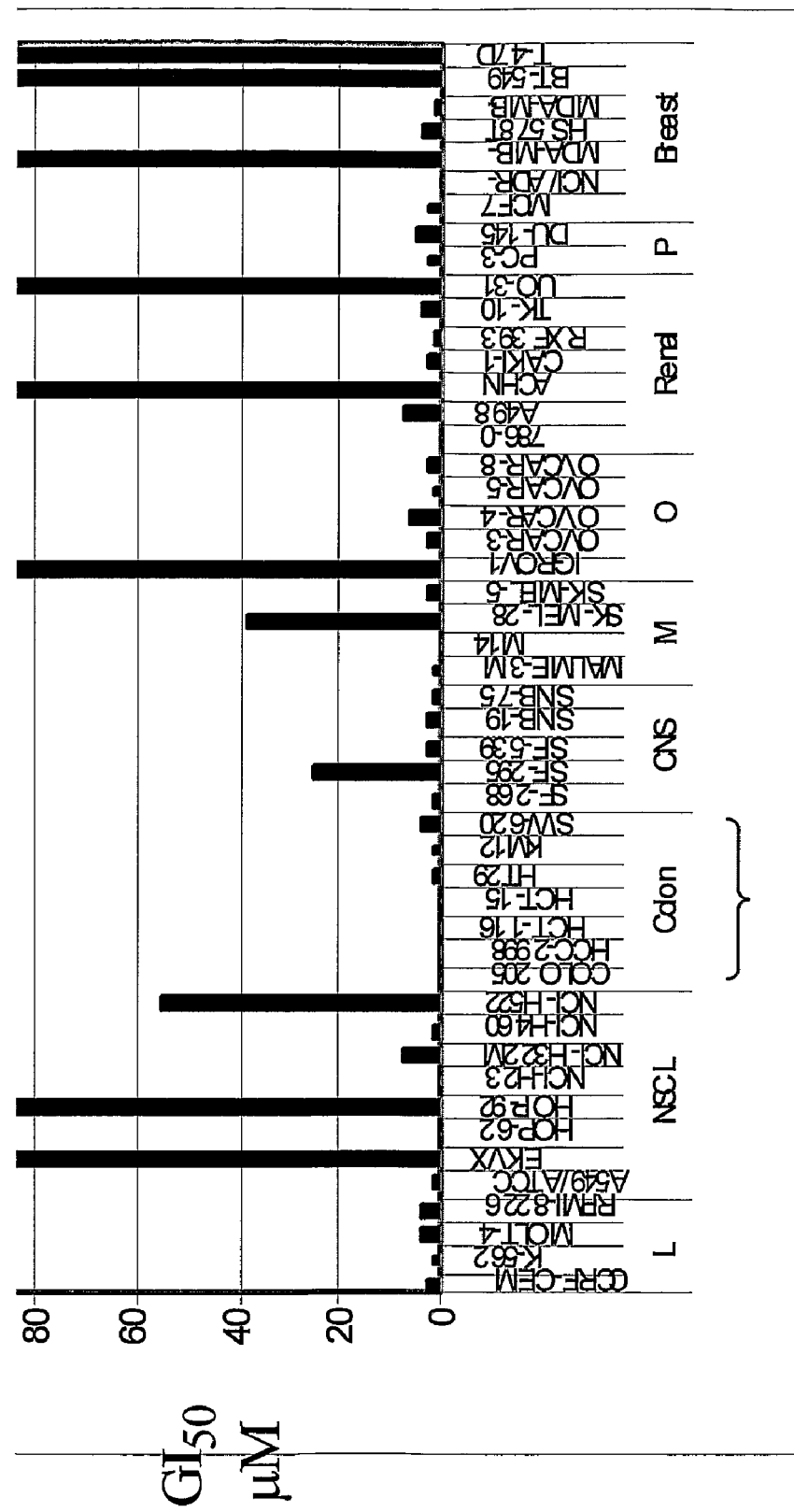
FIG. 1 Depicts the effects of SC-2-71 against the NCI 60 human cell lines ($GI_{50}$).

The aspects, advantages and/or other features of example embodiments of the invention will become apparent in view of the following detailed description, which discloses various non-limiting embodiments of the invention. It is to be understood that each specific element includes all technical equivalents that operate in a similar manner to accomplish a similar purpose.

Abbreviations

| | |
|---|---|
| 5FU- | 5-fluorouracil |
| CAM- | chick chorioallantoic membrane |
| CoMFA- | comparative molecular field analysis |
| HMEC- | human microvessel endothelial cell |
| HUVEC- | human umbilical vein endothelial cell |
| IL- | interleukin |
| LV- | leucovorin |
| MDR- | multidrug resistant |
| MMP- | matrix metalloproteinases |
| MVD- | microvessel density |
| Pgp- | P glycoprotein |
| Rr- | relative resistance |
| VEGF- | vascular endothelial growth factor |

Definitions

In describing and claiming example embodiments of the invention, the following terminology will be used in accordance with the definitions set forth below for the sake of clarity. However, the embodiments are not intended to be limited to this specific terminology. All of the definitions throughout this application, may relate to any of the embodiments of the inventions described herein, and are not limited to any particular embodiment(s) by virtue of their location within the specification, or otherwise.

As used herein, the articles "a" and "an" refer to one or to more than one, i.e., to at least one, of the grammatical object of the article. By way of example, "an element" means one element or more than one element. As used herein, "another" may mean at least a second or more.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine). In particular an analog is used to indicate that the structure of a compound is related to that of another compound, but whose chemical or biological properties may be different from the parent compound.

"Angiogenesis-associated" disease or disorder refers to a disease or disorder associated with aberrant angiogenesis or a disease or disorder reliant on angiogenesis. Changes in microvessel density are encompassed within the term "angiogenesis-associated."

"Anti-proliferative," as used herein, refers to the ability of a compound to impede or inhibit cell proliferation. As such, the compound may act directly on a cell or may act indirectly. For example, in the context of cancer, a cancer cell can be inhibited from proliferating by depriving it of blood supply. The term "anti-proliferative" does not refer to a particular mechanism by which proliferation is inhibited or impeded.

The term "cancer," as used herein, is defined as proliferation of cells whose unique trait—loss of normal controls—results new characteristics such as unregulated growth, lack of differentiation, local tissue invasion, and metastasis. Examples include, but are not limited to, breast cancer, prostate cancer, ovarian cancer, cervical cancer, skin cancer, melanoma, pancreatic cancer, colorectal cancer, renal cancer, leukemia, non small cell carcinoma, and lung cancer.

As used herein, a "derivative" of a compound refers to a chemical compound that may be produced from another compound of similar structure in one or more steps, as in replacement of H by an alkyl, acyl, or amino group.

The term "disrupt" as used herein refers to the ability of a compound of the invention to inhibit microtubules from polymerizing or the ability of a compound of the invention to induce at least partial depolymerization of microtubules.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology. As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound of the invention to reduce or impede a described function, such as cell proliferation, tumor growth, or angiogenesis. Inhibition is by at least 10%, more preferably by at least 25%, even more preferably by at least 50%, and even more preferably, the function is inhibited by at least 75%.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "subject" or "patient" of diagnosis or treatment is a mammal, including a human. The terms "subject" and "patient" are used interchangeably herein.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, an "effective amount" means an amount sufficient to produce a selected effect. For example, an effective amount of an antimicrotubule agent is an amount that disrupts the dynamic response of microtubulins.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer, as used herein, refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. Optionally substituted aryl includes aryl compounds having from zero to four substituents, and substituted aryl includes aryl compounds having one or more substituents. The term ($C_5$-$C_8$ alkyl)aryl refers to any aryl group that is attached to the parent moiety via the alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

Exemplary compounds contain one or more asymmetric centers in the molecule. A structure that does not designate the stereochemistry is to be understood as embracing all the various optical isomers, as well as racemic mixtures thereof Example compounds may exist in tautomeric forms and the invention includes both mixtures and separate individual tautomers. For example the following structure:

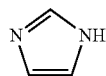

is understood to represent a mixture of the structures:

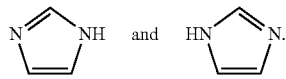

The term "pharmaceutically-acceptable salt" refers to salts which retain the biological effectiveness and properties of example compounds and which are not biologically or otherwise undesirable. In many cases, example compounds may be capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri- amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Example Embodiments

Thalidomide (shown below) was developed in the 1950s by Chemie Grunenthal of Germany as a non-toxic sedative. It was widely used to prevent morning sickness in pregnant women.

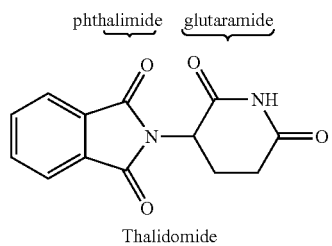

Thalidomide

In addition to its sedative effects in humans, an association was reported of teratogenic limb defects from maternal thalidomide usage. Aside from this serious teratogenic effect on the fetus, the drug does have therapeutic value: (1) for its immunosuppressive effect in the treatment of graft versus host disease; (2) in the treatment of leprosy; and (3) for inflammatory dermatoses. Furthermore, thalidomide has significant anti-angiogenic activity, and as a result, is finding more extensive clinical use in the treatment of various cancers, particularly in cancers having a poor prognosis due to microvessel density (e.g. multiple myeloma and prostate). Anti-angiogenic thalidomide derivatives have been previously described, including a derivative wherein the glutaramide ring is replaced with a phenyl group, leading to an active compound named, BROWN1.

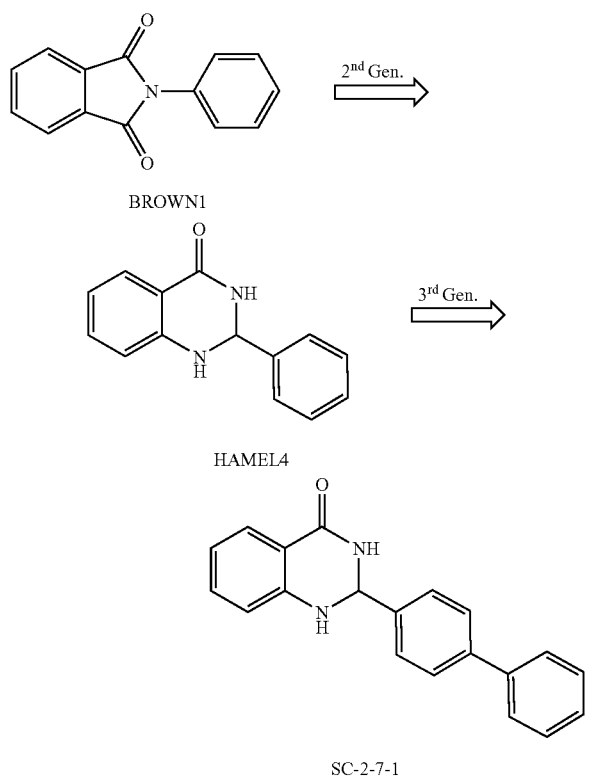

Second generation analogues were conceived by a ring expansion of the phthalimide ring, which resulted in the previously reported quinazolinone (HAMEL4; see published PCT application no. WO 02/086078A3, the disclosure of which is incorporated in its entirety herein). HAMEL4 has now been further optimized herein to generate novel compound SC-2-71, which as disclosed herein has enhanced efficacy (relative to HAMEL4) against various cancers, including solid tumors such as colon cancer.

In accordance with example embodiments, a compound is provided having the general Formula (I):

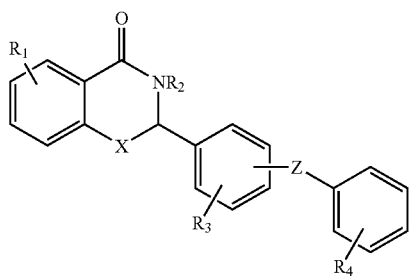

wherein $R_1$ is independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$);

wherein $R_3$ and $R_4$ are independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri- chloro and mono-, bi, and tri-methyl ($CH_3$), or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH $(CH_2)_n$)—, $CH_2$, $CHR_5$ and CO; wherein n is 1 or 2;

Z is selected from the group consisting of a bond, O, NH, S, CO, COO, $CH_2O$, $CH_2NH$, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring.

One of ordinary skill in the art would appreciate that compounds suitable for use and encompassed herein further include other analogs, derivatives, and modification of Formula I.

In accordance with example embodiments a compound of Formula I is provided wherein $R_1$, $R_3$ and $R_4$ are independently selected from the group consisting of H, halo, $C_1$-$C_4$ alkyl, $C_2$-$C_4$ alkenyl, $C_2$-$C_4$ alkynyl and $C_5$-$C_6$ aryl;

X is selected from the group consisting of $NR_5$, —(NH $(CH_2)_n$)—, $CH_2$ and CO;

n is 1 or 2;

Z is selected from the group consisting of a bond, O, NH, S, CO, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In further example embodiments, a compound of Formula I is provided wherein $R_1$, $R_3$ and $R_4$ are independently selected from the group consisting of H, halo and $C_1$-$C_4$ alkyl;

X is selected from the group consisting of $NR_5$, and CO;

Z is selected from the group consisting of a bond, CO and $C_1$-$C_4$ alkyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl. Furthermore it is anticipated that the hydrogen groups on the claimed compounds can be substituted with flourine atoms without significantly altering the activity of the parent compound.

In some aspects, $R_1$, $R_3$, and $R_4$ are each independently selected from the group consisting of mono-, bi-, and tri-chloro and mono-, bi, and tri-methyl ($CH_3$).

In certain embodiments, the compound is

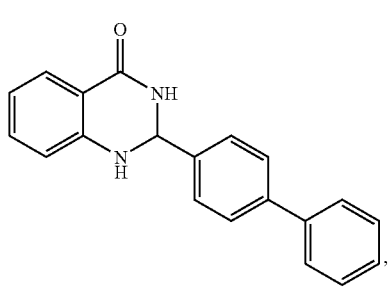

or an analog, derivative, or modification thereof

In some aspects, the analog, derivative, or modification of SC-2-71 is:

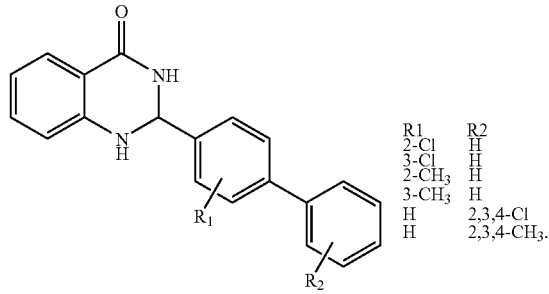

Aryl Substitution (Biphenyl)

In other aspects, $R_1$ and $R_2$ are independently mono-, di, or tri-chloro and mono-, di-, and tri-methyl ($CH_3$).

In accordance with example embodiments, the compound has the general structure:

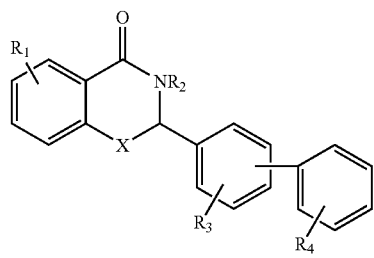

wherein $R_1$, $R_3$ and $R_4$ are independently selected from the group consisting of H, halo and $C_1$-$C_4$ alkyl;

X is selected from the group consisting of $NR_5$, —(NH$(CH_2)_n$)—, $CH_2$ and CO;

n is 1 or 2; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In some aspects, $R_1$, $R_3$, and $R_4$ are each independently selected from the group consisting of mono-, bi-, and tri-chloro and mono-, bi, and tri-methyl ($CH_3$).

In other embodiments of the compound has the general structure:

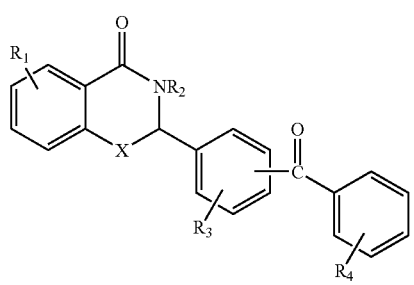

wherein $R_1$, $R_3$ and $R_4$ are independently selected from the group consisting of H, halo and $C_1$-$C_4$ alkyl;

X is selected from the group consisting of $NR_5$, —(NH$(CH_2)_n$)—, $CH_2$ and CO;

n is 1 or 2; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In some aspects, $R_1$, $R_3$, and $R_4$ are each independently selected from the group consisting of mono-, bi-, and tri-chloro and mono-, bi, and tri-methyl ($CH_3$).

In accordance with some embodiments, a compound is provided having the structure:

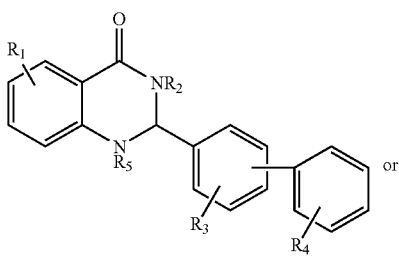

or

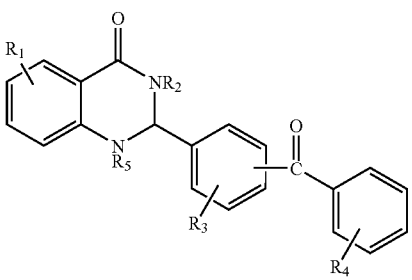

wherein $R_1$, $R_3$ and $R_4$ are independently selected from the group consisting of H, halo and $C_1$-$C_4$ alkyl, and $R_2$ and $R_5$ are independently selected from the group consisting of H, halo, $C_1$-$C_4$ alkyl, and $C_5$-$C_6$ aryl.

Other compounds provide herein include those of the formula:

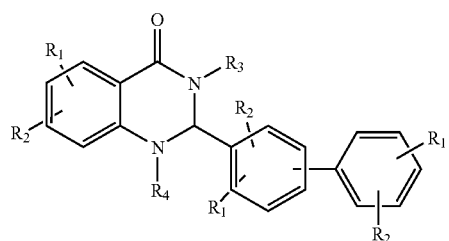

wherein $R_1$ and $R_2$ are independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri-chloro and mono-, bi, and tri-methyl ($CH_3$), and $R_3$ and $R_4$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In some embodiments of the invention, a compound has the following general structure:

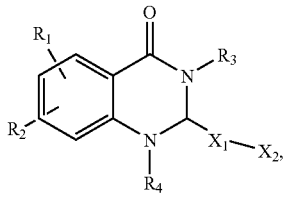

wherein $X_1$ and $X_2$ are each independently selected from the group consisting of heterocyclic, including thiophene, pyridine, pyrazine, pyrimidine, thiophene, furan, oxazole, and imidazole, further wherein $X_1$ and $X_2$ may independently comprise $R_1$ and $R_2$;

wherein $R_1$ and $R_2$ are independently selected from the group consisting of $NO_2$, H, halo, and $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, bi-, and tri- chloro and mono-, bi, and tri-methyl ($CH_3$); and wherein $R_3$ and $R_4$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In some embodiments, $X_1$ is thiophene. In some aspects the compound is:

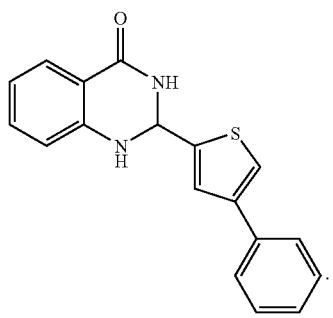

Certain aspects of the invention are directed to methods of treating an angiogenic-associated disease or condition by administering a compound or composition that inhibits angiogenesis. More particularly, certain embodiments of the invention are directed to a method of inhibiting undesired angiogenesis in a warm-blooded vertebrate, including humans. In some embodiments, the undesired angiogenesis may be associated with solid tumors, such as colon cancer. The method comprises administering to the human or animal a composition comprising an effective amount of a compound of the general Formula (I):

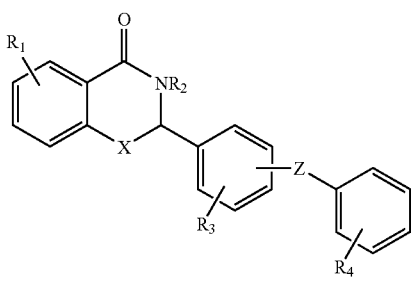

I wherein $R_1$, $R_3$ and $R_4$ are independently selected from the group consisting of H, halo and $C_1$-$C_4$ alkyl or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH$(CH_2)_n$)—, $CH_2$, $CHR_5$ and CO; wherein n is 1 or 2;

Z is selected from the group consisting of a bond, O, NH, S, CO, COO, $CH_2O$, $CH_2NH$, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring.

In some aspects, $R_1$, $R_3$, and $R_4$ are each independently selected from the group consisting of mono-, bi-, and tri-chloro and mono-, bi, and tri-methyl ($CH_3$).

In accordance with some embodiments, a compound of Formula I is provided wherein $R_1$, $R_3$ and $R_4$ are independently selected from the group consisting of H, halo and $C_1$-$C_4$ alkyl;

X is selected from the group consisting of $NR_5$, —(NH$(CH_2)_n$)—, $CH_2$ and CO; wherein n is 1 or 2;

Z is selected from the group consisting of a bond, O, NH, S, CO, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In a further embodiment a compound of Formula I is provided wherein $R_1$, $R_3$ and $R_4$ are independently selected from the group consisting of H, halo and $C_1$-$C_4$ alkyl;

X is selected from the group consisting of $NR_5$, and CO;

Z is selected from the group consisting of a bond, CO and $C_1$-$C_4$ alkyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

In some aspects of the invention, compounds of the invention include, but are not limited to:

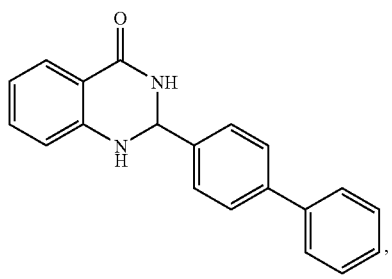

SC-2-71

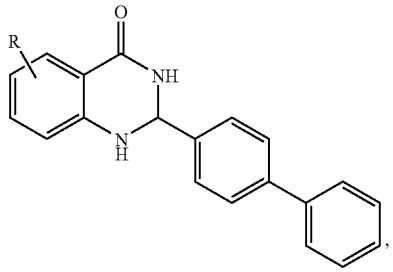

Aryl Substitution (fused ring)

R1
2 Cl, $CH_3$
3 Cl, $CH_3$
4 Cl, $CH_3$

-continued
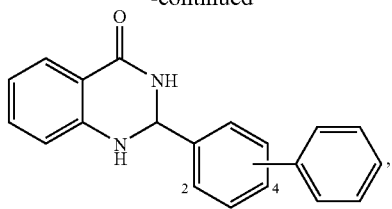
Phenyl Analogues/Isosteres
2- Ph
3- Ph
4- ≡
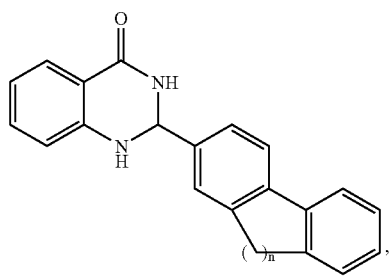
Biphenyl Rigid Analogues
n = 1,2
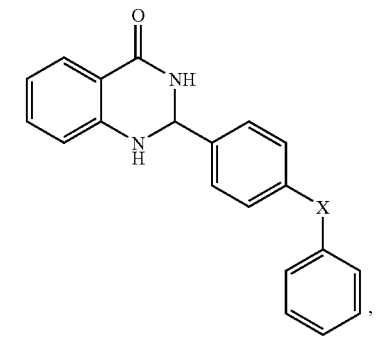
Spacer Insertion
X = CO, CH₂, C₂H₄
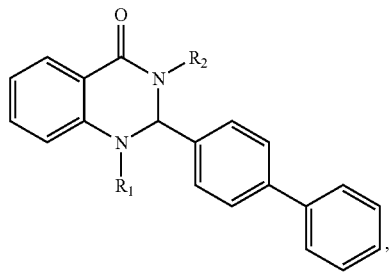
Amide/Amine Substitutions
| R1 | R2 |
|---|---|
| H | CH₃ |
| H | Ph |
| CH₃ | CH₃ |
| CH₃ | H |
| CH₃ | Ph |
| Ph | H |
| Ph | CH₃ |
| Ph | Ph |
-continued
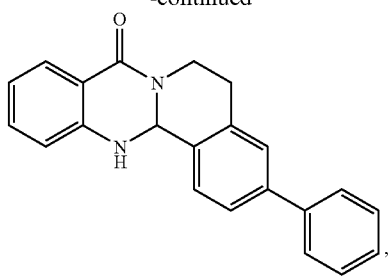
Rigid Analogues
(amide linked)
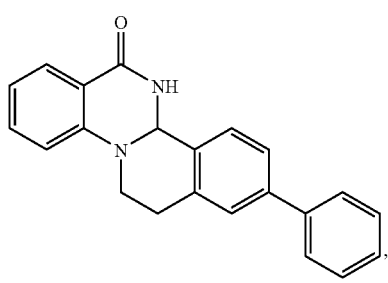
Rigid Analogues (amine)
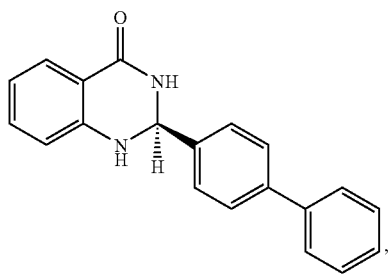
Chiral Analogue
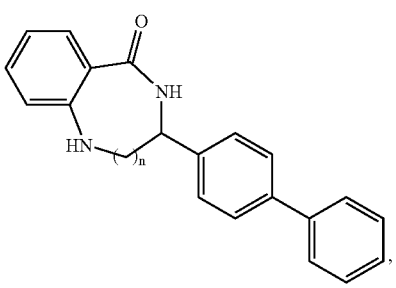
Ring Expansion
n = 1, 2

-continued

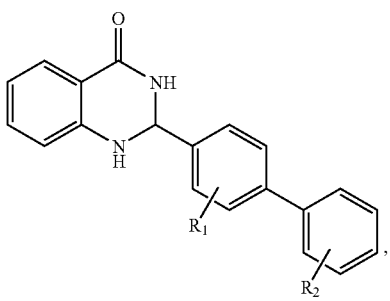

Aryl Substitution (Biphenyl)

| R1 | R2 |
|---|---|
| 2-Cl | H |
| 3-Cl | H |
| 2-CH3 | H |
| 3-CH3 | H |
| H | 2,3,4-Cl |
| H | 2,3,4-CH3 |

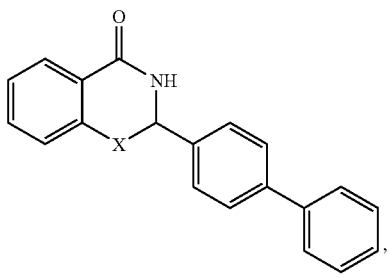

Group Homologues
X = C, N, C=O

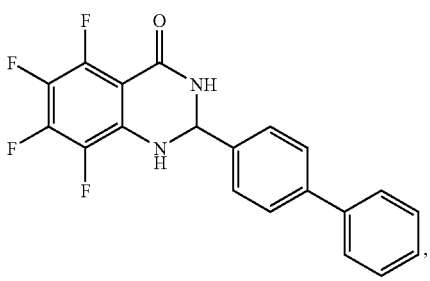

Tetrafluoro

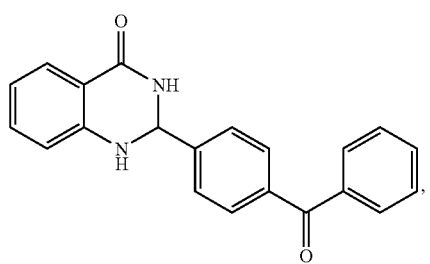

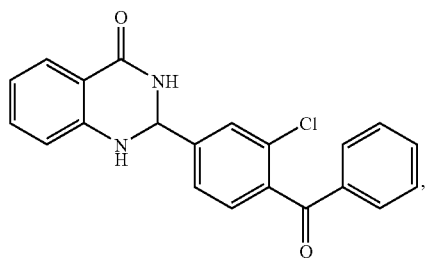

-continued

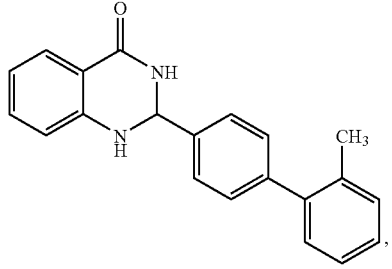

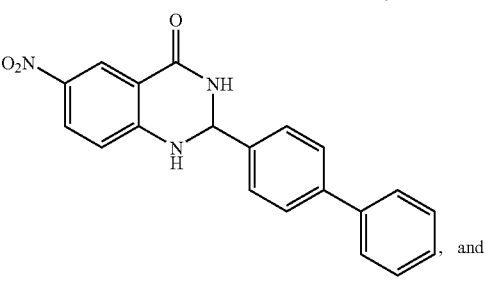

, and

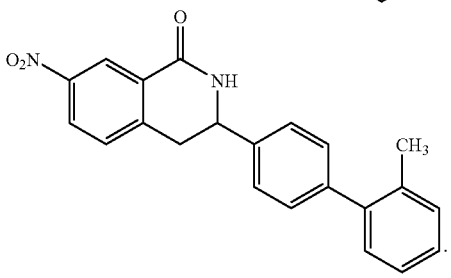

In accordance with some embodiments, example compounds can be formulated as pharmaceutical compositions by combining the compounds with one or more pharmaceutically acceptable carriers. These formulations can be administered by standard routes. In general, the combinations may be administered by the topical, transdermal, oral, rectal or parenteral (e.g., intravenous, subcutaneous or intramuscular) route.

When administered orally, the compounds may be administered for example, as a liquid solution, powder, tablet, capsule or lozenge. The compounds can be used in combination with one or more conventional pharmaceutical additives or excipients used in the preparation of tablets, capsules, lozenges and other orally administrable forms.

When administered parenterally, or by intravenous injection, in example embodiments derivatives can be admixed with saline solutions and/or conventional IV solutions. In addition, the combinations may be incorporated into biodegradable polymers allowing for sustained release of the compound. In some embodiments the delivery vehicle may be implanted in the vicinity of where drug delivery is desired, for example, at or near the site of a tumor. Biodegradable polymers suitable for use are known to the skilled practitioner and are described in detail, for example, in Brem et al., J. Neurosurg. 74:441-446 (1991).

The dosage of the active compound may depend on the condition being treated, the particular compound, and/or other clinical factors such as weight and condition of the subject being treated (e.g., human or animal) and the route of administration of the compound. It is to be understood that the methods herein have application for both human and veterinary use.

In some embodiments relating to oral administration to humans, a dosage of between approximately 0.1 to 300 mg/kg/day, or between approximately 0.5 and 50 mg/kg/day, or between approximately 1 to 10 mg/kg/day, may be generally sufficient.

It should be understood that in addition to the active anti-angiogenic compounds of Formula I, example compositions may include other agents conventional in the art including for example, solubilizing agents, inert fillers, diluents, excipients and flavoring agents.

In accordance with some embodiments a composition comprising a compound of Formula I may be used to inhibit angiogenesis. In some embodiments, the composition may be administered to treat a disease, disorder, or condition associated with excessive or undesirable angiogenesis, such as that associated with solid tumors. More particularly, microvessel density (MVD) or microvessel count within a tumor is a widely studied marker of angiogenesis. Patients whose tumors have a high MVD have a shorter survival than those with a low MVD. In fact, a correlation of increased microvessel density and poor prognosis has been found for several devastating solid tumors including colorectal cancer (Saclarides et al., Diseases of the Colon & Rectum. 37(9):921-6, 1994).

In some embodiments of the invention, a compound of the invention is used to inhibit a disease, disorder, or condition which is associated with increased angiogenesis or microvessel density. In accordance with other embodiments, compounds having the general structure of Formula I that exhibit anti-cancer and anti-angiogenic activity, are used to inhibit the growth of solid tumors.

The effects of 123 anticancer agents on the 60 cancer cell lines in the NCI's anticancer drug screen were evaluated for activity against cell lines with wild type or mutant p53 (see examples). Cell lines with mutant p53 were less sensitive to topoisomerase inhibitors, antimetabolites and DNA cross-linkers, as compared to cells with normal p53. The one group of chemotherapeutic agents that differed in this regard included anti-microtubule agents. These in vitro results are consistent with clinical results (Safran, et al., Cancer, 78: 1203-1210, 1996). Thus, it is believed that the compounds of Formula I may have enhanced efficacy against cancers that express an altered p53.

Exemplary compounds may be useful as anti-proliferative agents against cancer cells. In some aspects, the cancer cells include, but are not limited to, colon, multiple myeloma, breast, leukemia, cervical, central nervous system, non small cell carcinoma, melanoma, ovarian, and prostate cancer cells. In some aspects, the cancer may be a solid tumor. In other aspects, the cancer may be leukemia.

The effectiveness of the compounds of the invention in inhibiting tumor growth can be measured by numerous techniques known to those of skill in the art. Such techniques may include for example, the use of radiolabeled compounds, numerous radiographic imaging techniques, as well as physical measurement.

In some embodiments, the compounds of the invention are administered to a subject in a pharmaceutical composition further comprising a known chemotherapeutic agent. Chemotherapeutic agents are known to those of ordinary skill in the art, as are the doses to be used.

Another disease which can be treated in accordance with example embodiments is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Exemplary compounds may have use in treating a wide variety of diseases or conditions that are related to angiogenesis, including diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, pemphigold radial keratotomy, and corneal graph rejection. In other embodiments, diseases associated with corneal neovascularization can be treated by administering a composition comprising at least one compound of Formula I. Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitreitis, mycobacterial infections, Lyme's disease, systemic lupus erythematosus, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications.

The compounds of Formula I as described herein have been found to exhibit anti-microtubule activity.

Example embodiments are also directed to pharmaceutical compositions comprising at least one compound herein. More particularly, such compounds can be formulated as pharmaceutical compositions using standard pharmaceutically acceptable carriers, fillers, solubilizing agents and/or stabilizers known to those skilled in the art. For example, a pharmaceutical composition comprising a compound of the invention, or analog, derivative, or modification thereof, as described herein, may be used to administer the appropriate compound to a subject.

Pharmaceutical compositions comprising at least one compound are administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Intravenous injection or infusion may be used for example for the acute treatments. For maintenance regimens, the oral or parenteral, e.g. intramuscular or subcutaneous, routes may be used.

In accordance with some embodiments, a composition is provided that includes a compound of the invention, or an analog, derivative, or modification thereof, and albumin. More particularly, the composition may include an exemplary compound, a pharmaceutically acceptable carrier and 0.1-1.0% albumin. Albumin functions as a buffer and may improve the solubility of the compound. In other embodiments, albumin is not added.

In some embodiments, pharmaceutical compositions useful for practicing the invention may be administered to deliver a dose of between 1 ng/kg/day and 100 mg/kg/day. In other embodiments, pharmaceutical compositions useful for practicing the invention may be administered to deliver a dose of between 1 ng/kg/day and 100 g/kg/day.

Pharmaceutically acceptable carriers which may be useful in compositions include, but are not limited to, glycerol, water, saline, ethanol, and other pharmaceutically acceptable salt solutions such as phosphates and salts of organic acids. Examples of these and other pharmaceutically acceptable carriers are described for example, in Remington's Pharmaceutical Sciences (1991, Mack Publication Co., New Jersey).

Example pharmaceutical compositions may be prepared, packaged, or sold in the form of a sterile injectable aqueous or oily suspension or solution. This suspension or solution may be formulated according to methods known to those skilled in the art, and may include, in addition to the active ingredient, one or more additional ingredients such as dispersing agents, wetting agents, and/or suspending agents. Such sterile injectable formulations may be prepared for example, using a non toxic parenterally acceptable diluent or solvent, such as water or 1,3 butane diol. Other acceptable diluents and solvents include, but are not limited to, Ringer's solution, isotonic sodium chloride solution, and fixed oils such as synthetic mono- or di-glycerides.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of example pharmaceutical compositions provided herein are principally directed to pharmaceutical compositions that are suitable for administration to humans, it will be understood by the skilled artisan that such compositions are generally suitable for administration to animals of all sorts.

Modification of pharmaceutical compositions suitable for administration to humans to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals, including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient (e.g., compounds according to Formula I and analogs, derivatives, and modifications thereof), the pharmaceutically acceptable carrier, and any additional ingredients in a pharmaceutical composition may vary, depending for example, upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further include one or more additional pharmaceutically active agents. Particularly contemplated additional agents include anti-emetics and scavengers such as cyanide and cyanate scavengers.

According to example embodiments, controlled- or sustained-release formulations of a pharmaceutical composition may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed herein.

Some controlled-release formulations are designed to initially release an amount of drug that promptly produces the desired therapeutic effect, and gradually and continually release of other amounts of drug to maintain this level of therapeutic effect over an extended period of time. To maintain this relatively constant level of drug in the body, the drug may be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further include one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

Example formulations of pharmaceutical compositions suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet including the active ingredient may, for example, be made by compressing or molding the active ingredient, optionally with one or more additional ingredients. Compressed tablets may be prepared for example, by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these to provide for pharmaceutically elegant and palatable preparation.

Hard capsules including the active ingredient may be made using a physiologically degradable composition, such as gelatin. Such hard capsules include the active ingredient, and may further include one or more additional ingredients including, for example, an inert solid diluent such as calcium carbonate, calcium phosphate, or kaolin.

Soft gelatin capsules include the active ingredient may be made using a physiologically degradable composition, such as gelatin. Such soft capsules include the active ingredient, which may be mixed with water or an oil medium such as peanut oil, liquid paraffin, or olive oil.

Liquid formulations of a pharmaceutical composition, which are suitable for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further include one or more additional ingredients including, but not limited to, suspending, stabilizing, or dispersing agents. In some embodiments of formulations for parenteral administration, the active ingredient may be provided in dry (e.g., powder or granular) form for reconstitution with a suitable vehicle (e.g., sterile pyrogen free water) prior to parenteral administration of the reconstituted composition.

Example pharmaceutical compositions of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may include a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further include one or more of the additional ingredients described herein.

As used herein, "additional ingredients" may include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be apparent to or can be determined by the skilled artisan and will depend upon any number of factors, such as, but not limited to, the type and severity of the disease being treated, the type, and age of the subject, etc.

The invention also provides a pharmaceutical pack or kit including one or more containers having therein one or more of the ingredients of the pharmaceutical compositions of the invention. In accordance with some embodiments, a kit is provided for treating a subject in need of immuno-modulation. In some embodiments, the kit includes one or more of the SIP analogs and may also include one or more known immuno-suppressants.

Pharmaceuticals can be packaged in a variety of containers, e.g., vials, tubes, microtiter well plates, bottles, and the like. Other reagents can be included in the same or separate containers and provided with the kit; e.g., positive control samples, negative control samples, buffers, cell culture media, etc. Kits may also include instructions for use.

Compounds of the invention, which include, but are not limited to the example embodiments provided herein and analogs, derivatives, and modifications thereof, may be formulated and administered to a subject for treatment of any of the diseases and disorders described herein. However, the use of compounds of the invention should not be construed to include only the diseases and disorder described herein.

Moreover, compounds of the invention may be used for purposes other than treating diseases or disorders. For example, compounds of the invention may be used to determine the quantity and/or location of $\beta_{III}$ tubulin expression in a patient. The compounds provided herein preferentially bind to cells expressing $\beta_{III}$ tubulin and the compounds provide excitation and emission wavelengths that allow one to visualize areas having cells expressing $\beta_{III}$ tubulin. Visualization of compounds bound to cells expressing $\beta_{III}$ tubulin may be used to determine the location and/or extent of excessive or uncontrolled growth of cells.

Methods may include for example, administering at least one compound to a patient and determining the quantity and location of the compound within the patient by visualizing the compound within the patient. Visualization of the compound may provide an indication of the binding of the compound to cells that are actively expressing $\beta_{III}$ tubulin.

Accordingly, example methods include methods of determining the quantity and location of $\beta_{III}$ tubulin expression in a tissue, comprising administering a compound having the following formula (I) to the patient:

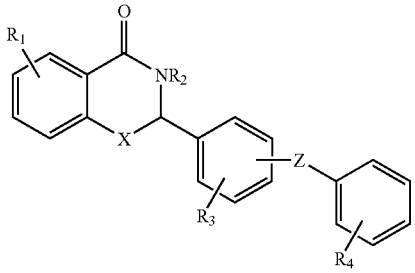

I wherein $R_1$, $R_3$, and $R_4$ are independently selected from the group consisting of $NO_2$, H, halo, $C_1$-$C_4$ alkyl, $C_2$-$C_4$ alkenyl, $C_2$-$C_4$ alkynyl, $C_1$-$C_4$ alkoxy, $C_5$-$C_7$ aryl, mono-, di- or tri-chloro, and mono-, di- or tri-methyl, or $R_3$ and $R_2$ taken together with the atoms to which they are attached form an optionally substituted heterocyclic fused ring, or $R_3$ and $R_4$ taken together with the atoms to which they are attached form an optionally substituted cycloalkyl fused ring;

X is selected from the group consisting of $NR_5$, —(NH $(CH_2)_n$)—, $CH_2$, $CHR_5$ and CO; wherein n is 1 or 2;

Z is selected from the group consisting of a bond, O, NH, S, CO, COO, $CH_2O$, $CH_2NH$, CONH, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl, or $R_3$ and $R_5$ taken together with the atoms to which they are attached form an optionally substituted heterocyclic fused ring, or an analog or derivative thereof, waiting a period of time after the administration and determining the presence and/or quantity of $\beta_{III}$ tubulin within the tissue, wherein the presence of the compound is indicative of the presence of $\beta_{III}$ tubulin within the tissue.

According to some embodiments, $R_1$, $R_3$ and $R_4$ may be independently selected from the group consisting of H, halo, $C_1$-$C_4$ alkyl, $C_2$-$C_4$ alkenyl, $C_2$-$C_4$ alkynyl and $C_5$-$C_6$ aryl;

X is selected from the group consisting of $NR_5$, —(NH $(CH_2)_n$)—, $CH_2$ and CO; wherein n is 1 or 2;

Z is selected from the group consisting of a bond, O, NH, S, CO, $C_1$-$C_4$ alkyl, $C_1$-$C_4$ alkenyl, and $C_1$-$C_4$ alkynyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

According to other embodiments, $R_1$, $R_3$ and $R_4$ may be independently selected from the group consisting of H, halo and $C_1$-$C_4$ alkyl;

X is selected from the group consisting of $NR_5$, and CO;

Z is selected from the group consisting of a bond, CO and $C_1$-$C_4$ alkyl; and $R_2$ and $R_5$ are independently selected from the group consisting of H, halo, $C_5$-$C_6$ aryl, $C_1$-$C_4$ alkyl, $C_1$-$C_4$ alkenyl, and $C_1$-$C_4$ alkynyl.

According to further example embodiments, the compound is

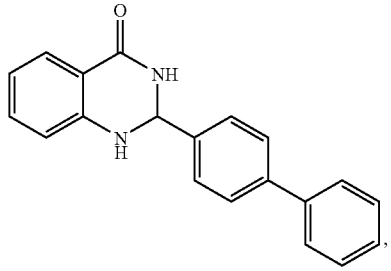

SC-2-71 or an analog, derivative, or modification thereof

The determined quantity of $\beta_{III}$ tubulin may be a relative quantity or it may be an absolute quantity. Methods may further include comparing the determined quantity (relative or absolute) of $\beta_{III}$ tubulin to a previously-determined amount of $\beta_{III}$ tubulin in the same tissue at a different time to determine a difference in expression of $\beta_{III}$ tubulin in the tissue.

In other embodiments, methods may include comparing the determined quantity (relative or absolute) of $\beta_{III}$ tubulin to a previously-determined amount of $\beta_{III}$ tubulin in different patients or to a schedule or range of $\beta_{III}$ tubulin expression. Such comparisons may assist in determining the extent of $\beta_{III}$ tubulin expression, which may assist in determining, for example, the extent of angiogenesis, neoplastic growth tumor growth, cancer or other disorder in the patient.

In these methods, the compound(s) may be administered by methods available to those skilled in the art, such as topical, oral, buccal, intravenous, intramuscular, intra-arterial, intramedullary, intrathecal, intraventricular, intraocular, transdermal, subcutaneous, intraperitoneal, intranasal, enteral, sublingual, vaginal, ophthalmic, pulmonary, and rectal methods. According to some embodiments, the compound(s) may be administered by injection.

According to example methods, detecting may include, but is not limited to, detecting the fluorescence emission of the compound. The wavelength of the detectable fluorescence emission wavelength may or may not be within the visible spectrum of light.

According to example embodiments, detecting may be performed using an angiogram. Detecting may also include photographing fluorescence emitted after illumination of the retina with blue light at a wavelength of about 490 nanometers.

According to some embodiments, methods may include waiting for a predetermined period of time after administration of the compound(s) to allow the compound to reach cells actively expressing $\beta_{III}$ tubulin. For example, the methods may include waiting from about 1 minute to about 4 hours after administration of the compound(s) for the compound(s) to reach to the area of interest and preferentially bind to cells expressing $\beta_{III}$ tubulin. By way of non-limiting example, methods may include waiting from about 11 minute to about 4 hours after administration of the compound(s) to a patient, to allow the compound to reach the retina and preferentially bind to blood vessels expressing $\beta_{III}$ tubulin. According to other embodiments, methods may include waiting less than one minute after administration of the compound or waiting longer than 4 hours after administration of the compound.

According to some embodiments, $\beta_{III}$ tubulin may be indicative of the presence and/or extent of an angiogenesis related disease or disorder selected from the group consisting of cancer, rheumatoid arthritis, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graph rejection, macular degeneration, sickle cell anemia, sarcoid, syphilis, pseudoxanthoma elasticum, Paget's disease, vein occlusion, artery occlusion, carotid obstructive disease, chronic uveitis/vitreitis, mycobacterial infections, Lyme's disease, systemic lupus erythematosus, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications.

According to some embodiments, the tissue of interest may be the retina or any portion thereof, such as, but not limited to the macula. The presence of $\beta_{III}$ tubulin within the retina, may therefore be indicative of the presence or extent of macular degeneration in the patient.

According to other embodiments, the tissue of interest may be normal or abnormal tissue, and the determination of quantity and location of $\beta_{III}$ tubulin within the tissue may be indicative of the presence or extent of neoplastic growth. Examples of tissues which can be analyzed using the compounds of the present invention include but are not limited to, ocular tissue, nerve tissue, mammary tissue, liver tissue, brain tissue, muscular tissue, lung tissue, bladder tissue, prostate tissue, colon tissue, vaginal tissue, uterine tissue, skin tissue, bone, spleen tissue, stomach tissue, pancreatic tissue, intestinal tissue and rectal tissue, to name a few. The tissue may or may not have been removed from a patient prior to administration of the compound(s) of the present invention.

In one particular embodiment, the compounds of the present invention may be administered directly or indirectly to any tissue suspected of having abnormal angiogenic activity and/or neoplastic growth. Thus, neoplastic growth, such as, but not limited to, malignant and/or benign tumors may be detected in accordance with these methods and may be any form of growth or abnormal condition for which $\beta_{III}$ tubulin expression may play a role. Examples of such conditions for which $\beta_{III}$ tubulin expression may play a role, include but are not limited to, multiple myeloma, breast cancer, prostate cancer, ovarian cancer, cervical cancer, skin cancer, melanoma, pancreatic cancer, colorectal cancer, renal cancer, central nervous system, leukemia, non small cell carcinoma, and lung cancer.

As with other embodiments, the methods may be applicable to situations where the patient or subject is a human or animal. The dosage amount and form of various compounds may vary depending on the type of patient (e.g., human vs. animal), as well as based on the gender, size and/or other factors. According to these methods, at least one compound may be administered to a patient in the form of a composition suitable for the method of administration.

One skilled in the art will readily appreciate that the present invention is well adapted to carry out the objects and obtain the ends and advantages mentioned, as well as those inherent therein. Additionally, the invention may be embodied in other specific forms without departing from the spirit or essential attributes thereof Any methods and materials similar or equivalent to those described herein can be used in the practice or testing of the present invention as would be apparent to those skilled in the art.

EXAMPLES

The following examples are provided for the purpose of illustration only and the invention should in no way be construed as being limited to these examples, but rather should be construed to encompass any and all variations which become evident as a result of the teachings provided herein.

Example 1

SC-2-71 Effects on Proliferation

SC-2-71 was evaluated against human cultured cell lines in the NCI Anticancer Drug Development Program. The data provided below in Table 2 reveals that SC-2-71 is a potent inhibitor of colon cancer proliferation with anti-proliferative activities ranging from 68 nM to 4 µM. This includes potent inhibition of colon cancer cells from primary tumors, distal metastasis and ascites fluid.

TABLE 2

$GI_{50}$ summary for human colon cell lines treated with SC-2-71

| | $GI_{50}$ Data (µM) | | | | | | |
|---|---|---|---|---|---|---|---|
| Compound | T29 | COLO205 | HCC-2998 | HCT-116 | HCT-15 | KM12 | SW-620 |
| SC-2-71 | 1 | .9 | 0.068 | 0.5 | 0.4 | 2 | 4 |
| Vincristine[a] | 0.11 | 0.12 | 0.11 | 0.12 | 0.14 | 0.12 | 0.11 |
| 5FU[a] | .7 | 7.2 | 1.4 | 4.0 | 5.8 | 11.1 | 26.2 |

[a]NCI data. 5FU = 5-Fluorouracil

Further grade III tumor cells (HCT116) were also significantly inhibited ($GI_{50}$=500 nM). In comparison to 5-FU (currently approved for stage III colon cancer), SC-2-71 was significantly more effective at inhibiting human colon cancer cell lines. SC-2-71 had similar potency as compared to Vincristine, a well known anti-mitotic agent. Altogether, this data establishes that SC-2-71 has therapeutically relevant anti-proliferative activity against human cultured colon cancer cells.

Furthermore, as indicated by the $GI_{50}$ data obtained from the National Cancer Institute (NCI) and presented in FIG. 1, SC-2-71 also exhibits toxicity to a wide range of tumor cell lines. The smallest bars represent the cell lines for which SC-2-71 had the most potent anti-proliferative effect. Several interesting findings are evident. First, SC-2-71 can potently inhibit several types of cancers in the nanomolar range (the lowest GI$_{50}$ (colon HCC2998)=68 nanomolar). Second, the differential response to SC-2-71 by the cancer cell lines demonstrates that SC-2-71 is not toxic to every cell type (i.e. several GI$_{50}$'s are greater than 100 μM). Third, SC-2-71 does not have to be metabolically activated like thalidomide to have anti-cancer activity, since it is directly toxic when applied to cancer cells.

Figure 2A:
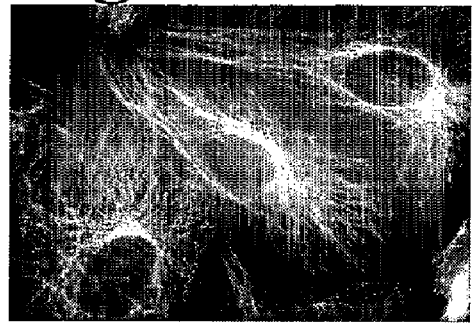
FIGS. 2A and 2B Depict the microtubule depolymerizing effects of SC-2-71 in A-10 cells.
Figure 2B:
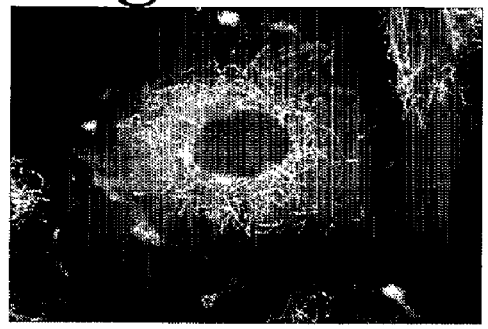

The microtubule disrupting effects of SC-2-71 were detected in a cell based phenotypic screen FIGS. 2A and 2B. SC-2-71 was Observed to cause dramatic reorganization of the interphase microtubule network, similar to the effects of vinblastine. While vehicle treated cells exhibit a normal filamentous microtubule array (FIG. 2A), SC-2-71 caused a concentration dependent loss of cellular microtubules. This effect is consistent with the effects observed from other microtubule depolymerizers. In addition to microtubule loss, treatment of the cells with SC-2-71 resulted in extensive micronucleation. This is also a hallmark of microtubule disrupting compounds. Depolymerization of interphase microtubules is a classic response of cells to relatively high concentrations of microtubule disruptors such as the vinca alkaloids. However, a large body of evidence suggests that at the lowest effective cytotoxic concentrations, the ability of these compounds to interrupt normal microtubule dynamics (and not changes in the tubulin polymer) causes mitotic arrest and subsequent apoptosis (Jordan, M.A., Curr. Med. Chem. 2:1-17, 2002).

Figure 3A:
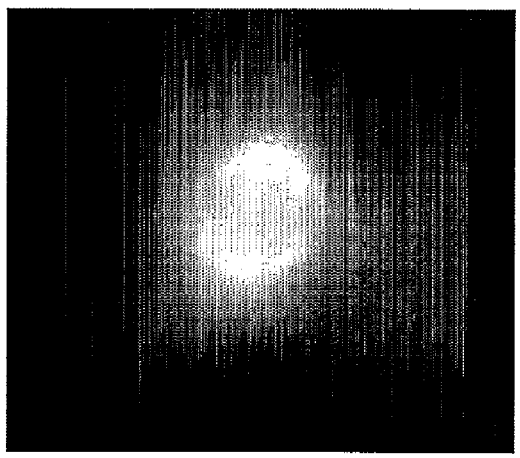
FIGS. 3A and 3B Demonstrate abnormal mitotic spindles initiated by low micromolar concentrations of SC-2-71 in HeLa cells.
Figure 3B:
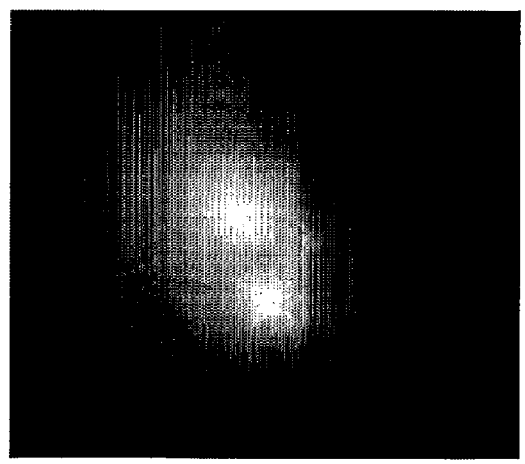

The ability of SC-2-71 to initiate mitotic accumulation and the formation of abnormal mitotic spindles was evident in both A-10 and HeLa cells at concentrations that did not cause dramatic changes in interphase microtubules. In HeLa cells, SC-2-71 causes the formation of abnormal mitotic spindles and mitotic accumulation at low micromolar concentrations (FIGS. 3A and 3B).

The effects of SC-2-71 on cell cycle progression were determined using flow cytometry techniques. MDA-MB-435 cells were treated with 3 μM SC-2-71 for 18 h, stained with Krishan's reagent and DNA content analyzed. The results (FIG. 4) show distinct mitotic accumulation consistent with interruption of normal mitotic spindle function and mitotic arrest.

The anti-proliferative activity of SC-2-71 as shown in Table 3 was evaluated using the SRB assay and it was found to have good potency against a reference cell line, MDA-MB-435. Analogues of SC-2-71 were tested for the ability to disrupt microtubules and for potency against MDA-MB-435. These tubulin depolymerization studies revealed that SC-2-71 potently inhibited tubulin polymerization (50% at 5 μM). The activities of several analogues of SC-2-71 that have microtubule disrupting activity, as defined by greater than 50% microtubule loss at 30 μM, are presented in Table 3. The data indicates that certain derivatives of SC-2-71 have even higher anti-microtubule activity (see compounds SC-5-87 and SC-5-121).

TABLE 3

Effects of analogues on Pgp expressing cells and tubulin polymerization.

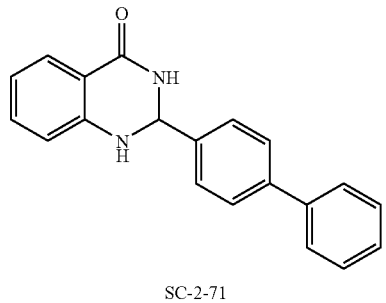

SC-2-71

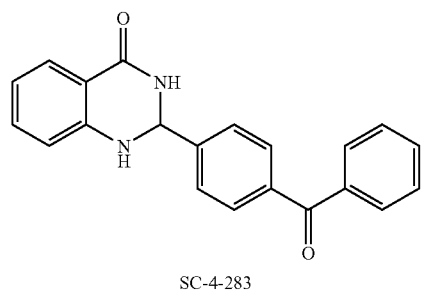

SC-4-283

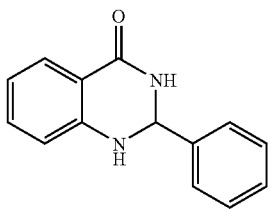

HAMEL4

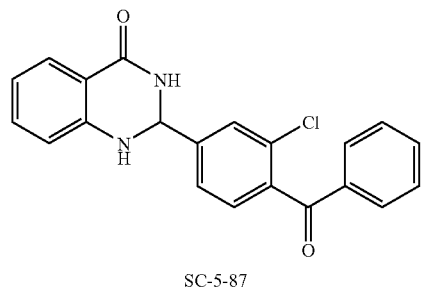

SC-5-87

TABLE 3-continued

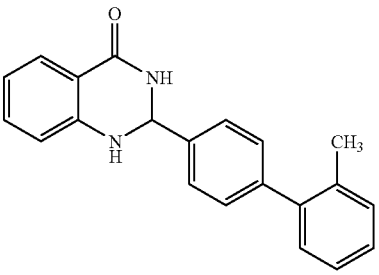

SC-5-121

| Compound | MDA-MB-435 Cells (IC$_{50}$ μM) | NCI/ADR Cells (Pgp expressing) (IC$_{50}$ μM) | Rr value | Microtubule activity (% depolymerization) |
|---|---|---|---|---|
| SC-2-71 | 0.61 ± 0.1 | 1.80 ± 0.11 | 2.95 | 50% at 5 μM |
| SC-4-283 | 0.90 ± 0.3 | | | 50% at 5 μM |
| HAMEL4 | 1.95 ± 0.4 | 3.19 ± 0.23 | 2.0 | 50% at 5 μM |
| SC-5-87 | 0.26 ± 0.02 | 0.76 ± 0.01 | 2.9 | 90% at 5 μM |
| SC-5-121 | 0.6 ± 0.1 | 0.88 ± 0.03 | 1.2 | 90% at 5 μM |

The ability of anti-microtubule/anti-angiogenesis compounds to circumvent Pgp may provide significant advantages for therapy of drug resistant tumors. The ability of SC-2-71 analogues to inhibit the proliferation of the Pgp expressing cell line NCI/ADR is demonstrated by the data provided in Table 3. Relative resistance (Rr) values can be calculated by dividing the IC$_5$ of the sensitive cell line by the IC$_{50}$ of the resistant cell line. The Rr value for taxol in the NCI/ADR (Pgp expressing) and MDA-MB-435 (Pgp deficient) cell lines is 827(Tinley, et at., Cancer Res. 63:1538-1549, 2003b). The Rr values for the present SC-2-71 analogues range from 1.3 to 2.9 strongly suggesting that they are poor substrates for transport by Pgp, and thus should be more effective agents against Pgp mediated multi-drug resistance.

Example 2

Comparative Molecular Field Analysis (COMFA) of SC-2-71 and Tubulin Polymerization CoMFA is a powerful ligand based discovery methodology to identify important relationships between steric and electrostatic molecular properties and biological data. A β-tubulin CoMFA has been developed that resulted in models which were predictive of both tubulin polymerization and [$^3$H] colchicine binding for a large set of β-tubulin inhibitors (Brown, et al., Bioorganic and Medicinal Chemistry, 8:6: 1433-1441, 2000). This study produced the first predictive models for multiple structural types including combretastatins, colchicine and podophyllotoxin. More recently, this CoMFA model was used to identify and predict the β-tubulin depolymerization activity of SC-2-71. The CoMFA model predicted that SC-2-71 would be a potent inhibitor of tubulin polymerization as was previously reported for the parent HAMEL4 compound (Hour et al., Journal of Medicinal Chemistry, 43:23:4479-87, 2000).

SC-2-71 Inhibits β-tubulin Polymerization

Analogues of SC-2-71 were tested for the ability to disrupt microtubules, and for potency against MDA-MB-435. These tubulin depolymerization studies revealed that SC-2-71 potently inhibited tubulin polymerization (50% at 5 μM). The activities of several analogues of SC-2-71 that have microtubule disrupting activity, as defined by greater than 50% microtubule loss at 30 μM, are presented in Table 4. The data indicates that certain derivatives of SC-2-71 have even higher anti-microtubule activity (see compounds SC-5-87 and SC-5-121).

It is believed that the anti-proliferative activity of the responding cell lines to SC-2-71 treatment is due to a difference in tubulin isotype expression in the responding cells. In fact, a proteomic study revealed that class III tubulin (III) is upregulated in HT29 colon cancer cells (Braguer et al., British Journal of Cancer, 80(8):1162-8, 1999). This cell line was very sensitive to SC-2-71 (GI$_{50}$=1 μM).

Example 3

Investigating the SC-2-71 Mechanism of Action

Figure 6A:
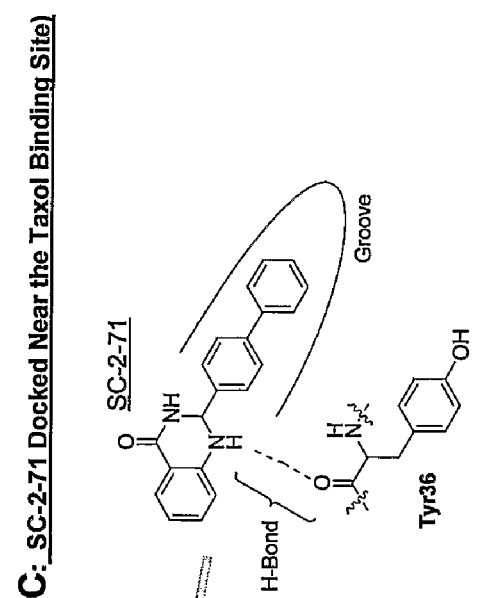
FIGS. 6A, 6B, and 6C Demonstrate the docking of SC-2-71 into the $\Gamma_{III}$ homology model.
Figure 6B:
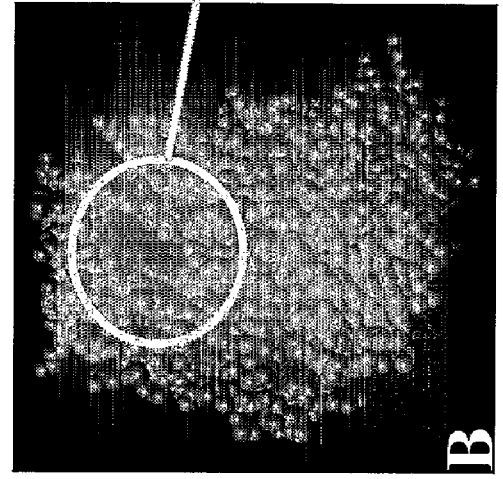
Figure 6C:
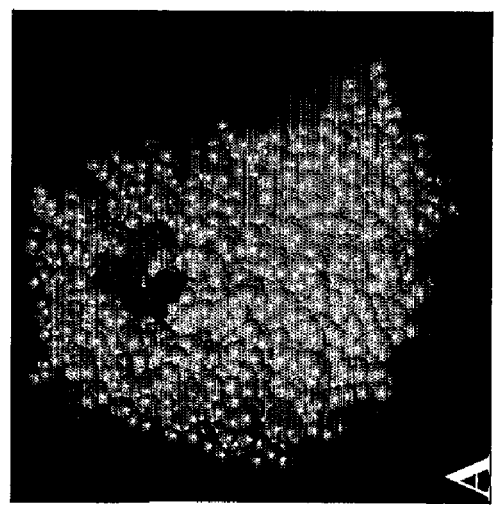

A 96% sequence homology (identity) exists between the x-ray structure sequence of β-tubulin (bovine brain) and β$_{III}$ (human) (see FIG. 5). With this high level of homology, the present inventor embarked on developing a protein model of human β$_{III}$ (FIG. 6B). Using the BIOPOLYMER module within SYBYL the inventor threaded the sequence in FIG. 5 into the reported x-ray structure to create the homology model of β$_{III}$ human tubulin (FIG. 6). The inventor then took the homology model of β$_{III}$ and flexible docked SC-2-71 into it using the FlexX/C-Score module within SYBYL (FlexX was developed at the German National Research Center for Information Technology (GMD), and is distributed by Tripos Inc., St. Louis Mo.; ww.tripos.com/software/flexx.html). SC-2-71 docks right into the area of greatest amino acid difference near the taxol and colchicine binding sites (FIGS. 6B and 6C). Overlap of the homology with the x-ray structure revealed that changes in amino acids resident in the β$_{III}$ protein near the taxol and colchicine binding sites could impart selective binding to SC-2-71. One important hydrogen bond was noted between tyrosine 36 and the amine portion of SC-2-71. Comparison of predicted binding affinities to β$_{III}$ tubulin suggested the rank order of SC-4-283>SC-2-71. This order was experimentally confirmed by tubulin depolymerization experiments in Table 3.

Figure 7:
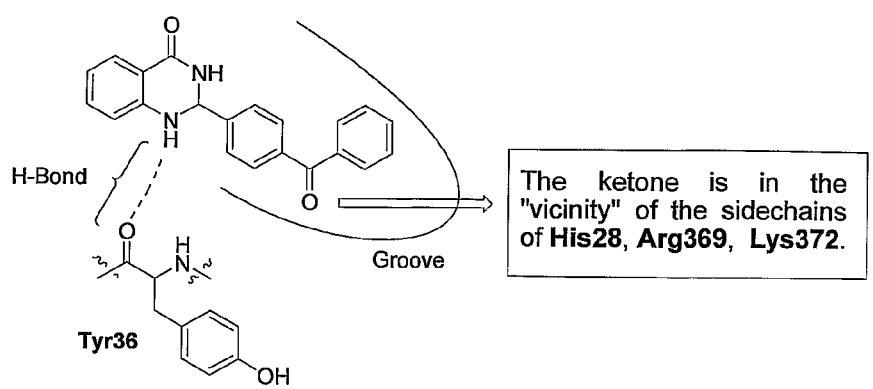
FIG. 7 Demonstrates the flexible docking of the potential photoaffinity label SC-4-283.

The model described herein was used to customize and design SC-4-283, a potential photoaffinity ligand of SC-2-71 (FIG. 7). The ketone is within a few angstroms of the sidechains of His28, Arg369, and Lys372. Therefore, these amino acids may provide potential reaction sites for imine formation. With this in mind, SC-4-283 was synthesized as a benzophenone photoaffinity label of SC-2-71 in an effort to elucidate and confirm the binding domain of SC-2-71. SC-4-283 was evaluated for inhibition of tubulin polymerization and found it to have improved inhibitory activity in relation to SC-2-71 (Table 4) as the inventor predicted. The inventor's model has allowed him to 1) assign priority of synthesis to new ligands based on rank of the ligand's predicted affinities to β-tubulin, 2) design potential affinity labels, and 3) propose labeling, digest and sequence analysis to validate their hypothesis.

Example 4

Inhibitory Effects of SC-2-71 on Endothelial Cell Proliferation In vitro and In vivo Without wishing to be bound by any particular theory, strategies and experiments are described herein pertaining to developing an anti-cancer strategy of simultaneously inhibiting endothelial and cancer cells. Compounds that target cellular microtubules have recently been found to exhibit anti-angiogenic activities and this may contribute to their antitumor and anticancer efficacies (Miller, et al., J. Clin. OncoL 19:1195-1206, 2001). The taxanes, taxol and docetaxel, vinblastine, vincristine and 2-methoxyestradiol all have anti-angiogenic activity in vivo. SC-2-71 inhibited Human Microvessel Endothelial Cell (HMEC; $IC_{50}$ of 20 µM) and Human Umbilical Vein Endothelial Cells (HUVEC; $IC_{50}$ of 1.6 µM proliferation (see Table 4). SC-2-71's ability to inhibit angiogenesis in an in vivo model was then examined.

TABLE 4

Inhibitory effects of SC-2-71 on endothelial cell proliferation.

| Compound | $HMEC^b$ $IC_{50}$ (µM) | $HUVEC^c$ $IC_{50}$ (µM) |
|---|---|---|
| SC-2-71 | 20 ± 5 | 1.66 ± 0.5 |

[a] All experiments were run in triplicate, and the ± values represent the SEM
[b] Human Microvessel Endothelial Cells
[c] Human Umbilical Vein Endothelial Cells SC-2-71 inhibits the Growth of Blood Vessels on the Chick Chorioallantoic Membrane (CAM) Model.

Figure 8A:
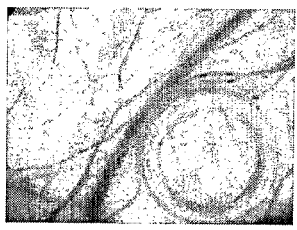
FIG. 8 depicts a chorioallantoic membrane (CAM) assay illustrating the anti-angiogenic effects of SC-2-71.
Figure 8B:
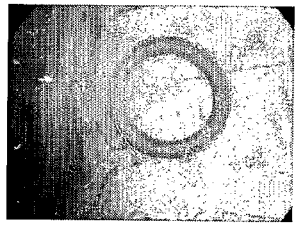
Figure 8C:
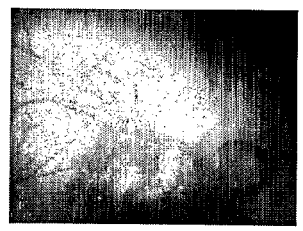
Figure 9:
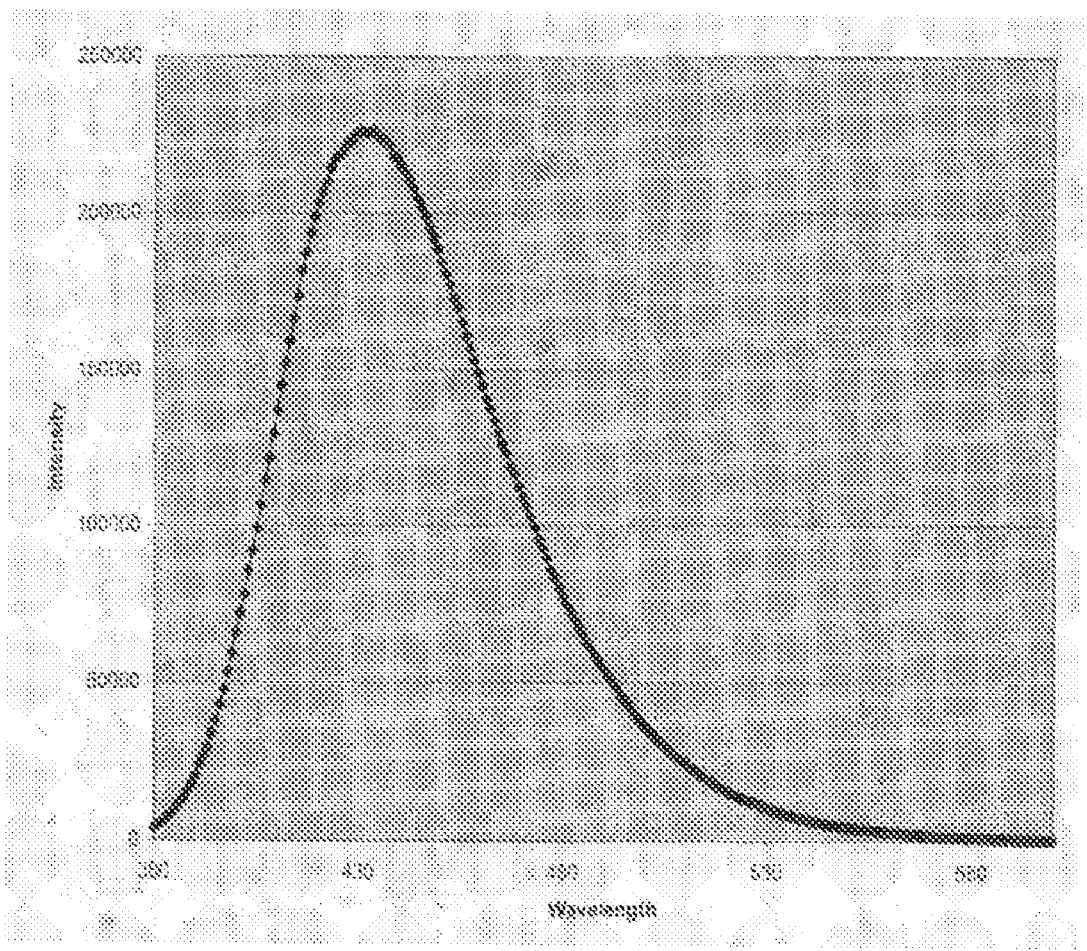
FIG. 9 depicts the fluorescence emission spectrum of GMC-5-193. The spectrum was analyzed at 350 nm excitation. Peak emission wavelength was at 433 nm.
Figure 10:
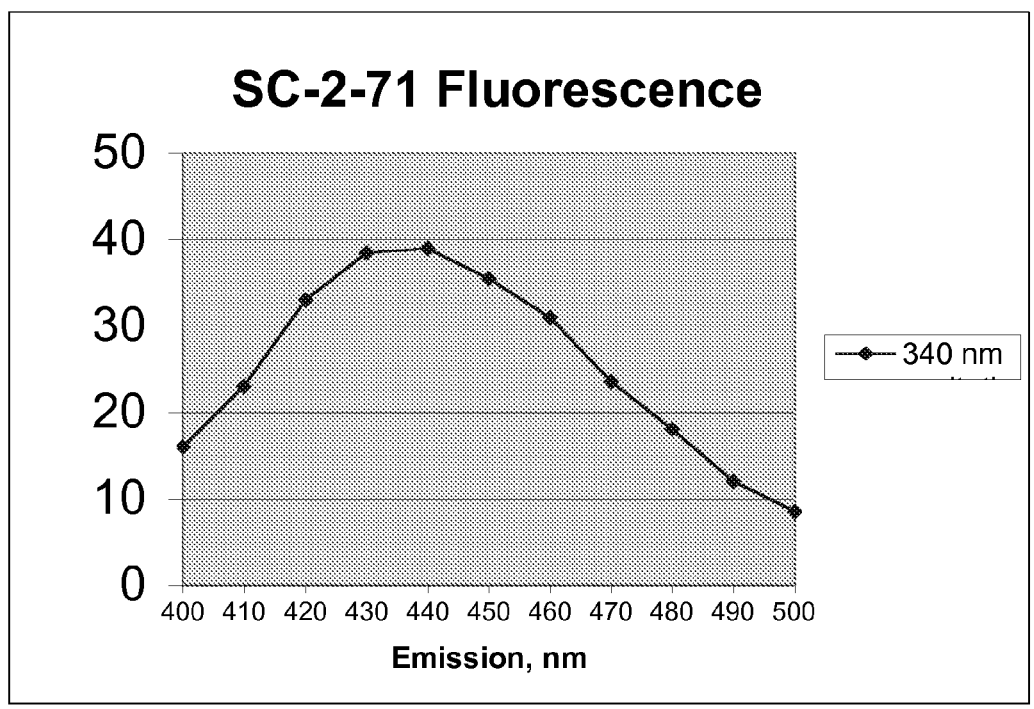
FIG. 10 depicts the fluorescence emission spectrum of SC-2-71. The spectrum was analyzed on an Aminco-Bowman spectrofluorometer at 340 nm excitation with 5.5 nm band pass using 150 µM SC-2-71 in ethanol. Peak emission wavelength was at 440 nm.

SC-2-71 (100 µM) inhibited a translational model of blood vessel growth in vivo (CAM, FIG. 8, panel B and C) as compared to control (FIG. 8, panel A). This strongly establishes that SC-2-71 has anti-angiogenic activity. Further it raises the question as to the expression level of $β_{III}$ tubulin in HMECs.

A summary of the results obtained with SC-2-71 is as follows:

SC-2-71 is a potent inhibitor of colon cancer proliferation with anti-proliferative activities ranging from 68 nM to 4 µM;

In comparison to 5-FU (currently approved for stage III colon cancer), SC-2-71 was significantly more effective at inhibiting human colon cancer cell lines;

SC-2-71 is a microtubule depolymerizing agent;

SC-2-71 caused dramatic reorganization of interphase microtubule networks, similar to the effects of vinblastine;

SC-2-71 causes the formation of abnormal mitotic spindles and mitotic accumulation at low micromolar concentrations;

SC-2-71 was a poor substrate for transport by Pgp.

A homology model of $β_{III}$ human tubulin was developed and used to 1) prioritize synthesis and 2) design a potential photoaffinity label. SC-4-283 was synthesized as a benzophenone photoaffinity label of SC-2-71 and found to also be a potent inhibitor of tubulin polymerization. SC-2-71 inhibits the proliferation of human microvessel and umbilical vein endothelial cells. SC-2-71 inhibits the growth of blood vessels in an in vivo model of angiogenesis.

Example 5

Synthesis of SC-2-71 and Derivative Compounds

SC-2-71 and analogues were synthesized in accordance with the following schemes by condensing anthranilamide with an appropriately substituted benzaldehyde derivative as shown in Scheme 1. Recrystallization of the crude solids from absolute ethanol afforded the pure products listed.

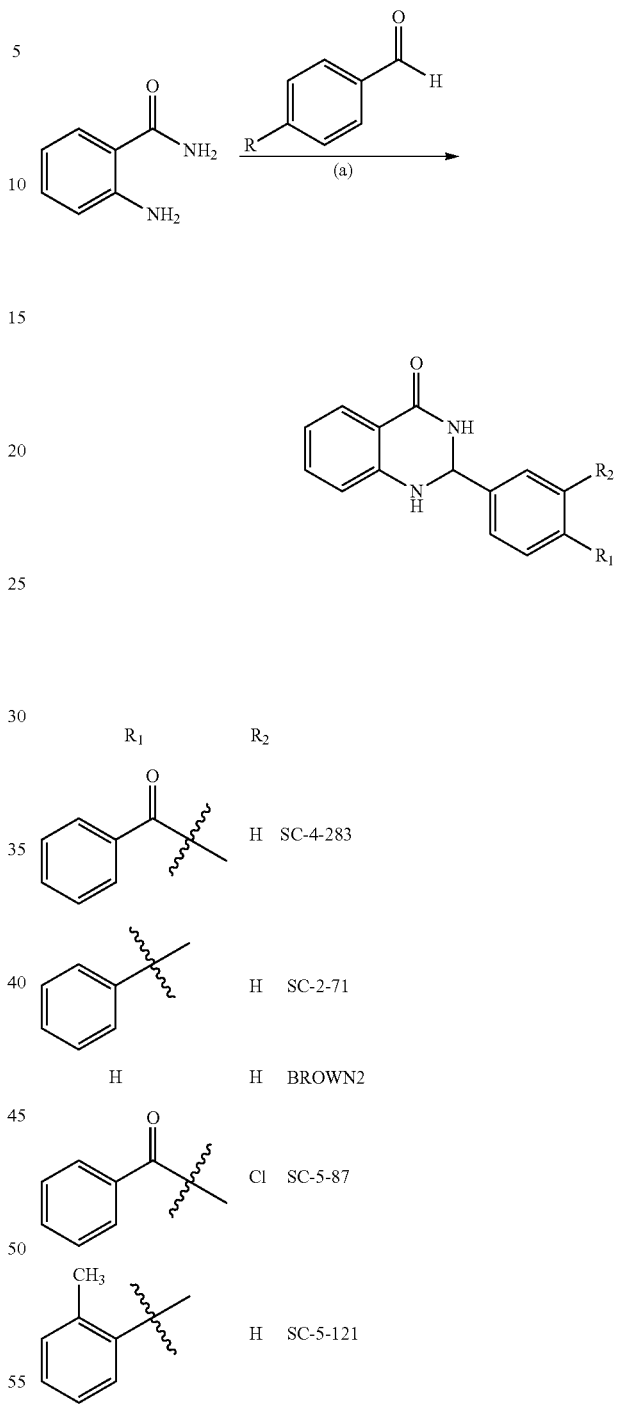

Scheme 1. Synthetic route for SC-2-71 and analogues.

[a] Reagents: (a) $CH_3CN$, AcOH (cat.), reflux 5-8 hrs

Compounds designed to optimize SC-2-71.

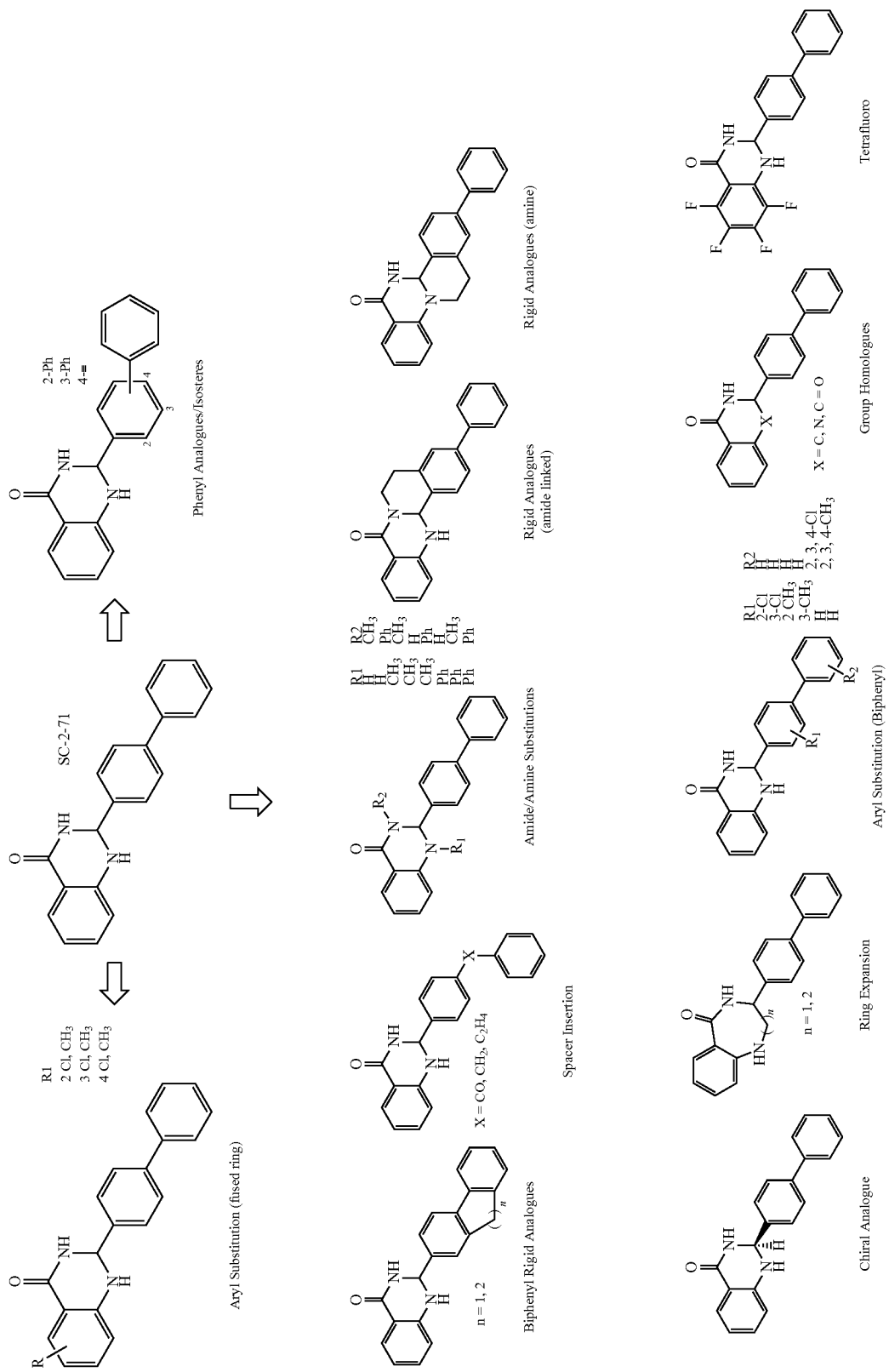

Other compounds may include:

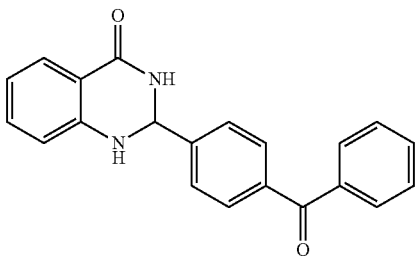

SC-4-283
m.p. = 209-211° C.
$^1$H NMR, $^{13}$C NMR, NCI: Declined

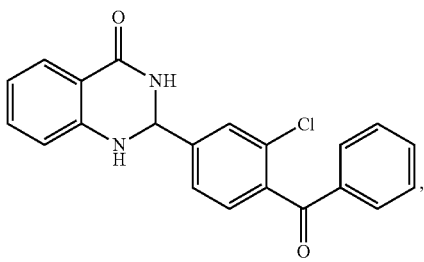

SC-5-87
m.p. = 177-179° C.
$^1$H NMR, $^{13}$C NMR, NCI: 60-cell

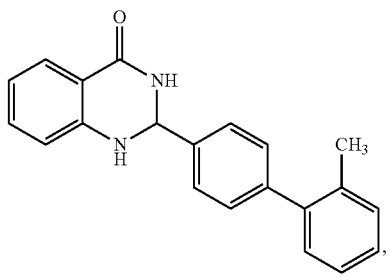

SC-5-121
m.p. = 169-171° C.
$^1$H NMR, $^{13}$C NMR, NCI: 60-cell

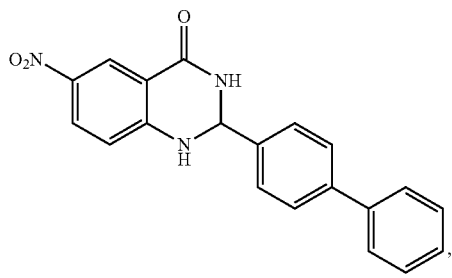

GMC-5-93
m.p. = 263-265° C.
$^1$H NMR, $^{13}$C NMR, NCI: Declined

-continued

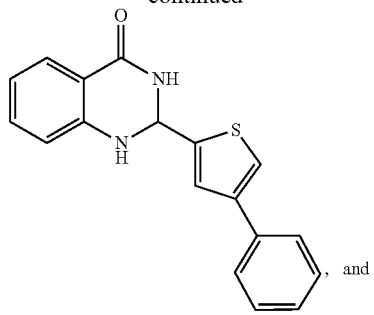

GMC-5-103
m.p. = 228-230° C.
$^1$H NMR, $^{13}$C NMR, NCI:

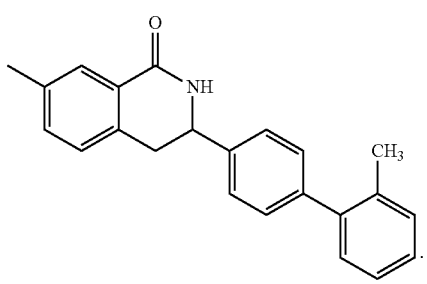

GMC-5-193
m.p. = 261-252° C.
$^1$H NMR, $^{13}$C NMR, NCI: 60-cell

The compounds described above also all have compelling in vitro data demonstrating their effects against colon and breast cancer. The compounds described herein may also be potent tubulin inhibitors and displace $^3$H-colchicine (data not shown).

Many of the starting aldehydes needed to complete the synthesis of the analogues of SC-2-71 are not commercially available. A brief outline of the synthesis of several of these important intermediates is provided below.

Scheme 2.

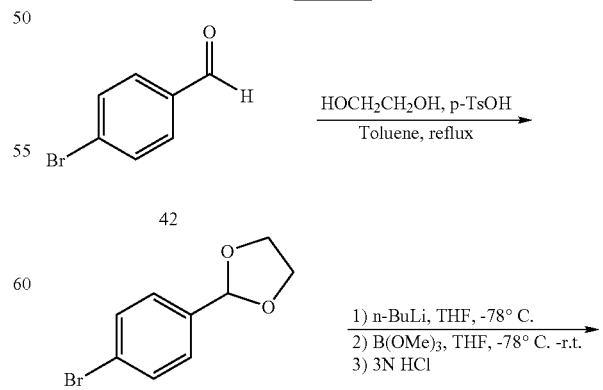

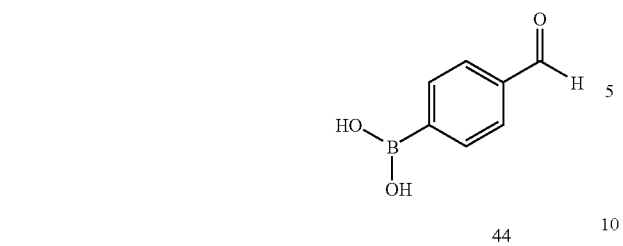

44

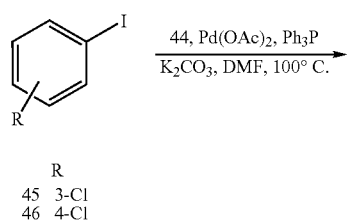

R
45  3-Cl
46  4-Cl

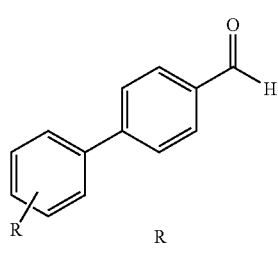

R
47  3-Cl
48  4-Cl

Example 6

Other Syntheses

A method for synthesis of the important synthetic intermediate 4-formylphenylboronic acid 44 with an acetal protection of 4-bromobenzaldehyde 42 is proposed. The resulting acetal will be converted to the trimethylborate and deprotected to afford the boronic acid 44. Key aldehydes 47 and 48 will be obtained under Suzuki coupling conditions using 44 and the appropriate substituted iodobenzene (Scheme 2).

Scheme 3.

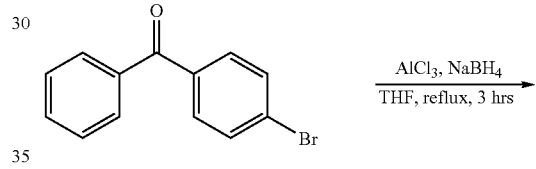

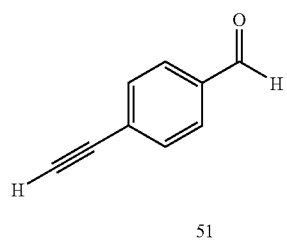

51

The synthesis of 4-ethynylbenzaldehyde 51 using a modified Castro-Stephens/Sonogashira coupling of 4-iodobenzaldehyde and trimethylsilylacetylene (Scheme 3) is proposed. Treatment of this aldehyde with potassium carbonate in methanol at room temperature should afford aldehyde 51. The plan for the synthesis of aldehyde 57 (4-benzoylbenzaldehyde) involves reducing 4-bromobenzophenone 52 and protecting the resulting secondary alcohol 53 with TBS to give 54. After the formylation of 54, 56 is deprotected and oxidized to the final aldehyde 57 (Scheme 4). In this same manner, the inventor plans to install a formyl group onto the aryl bromide 58 to give 59 (Scheme 5).

Scheme 4.

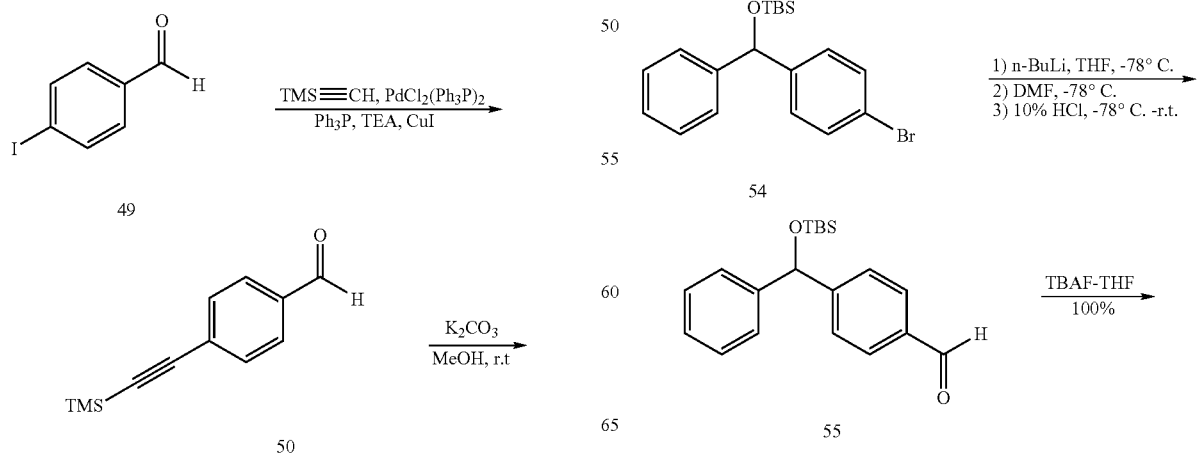

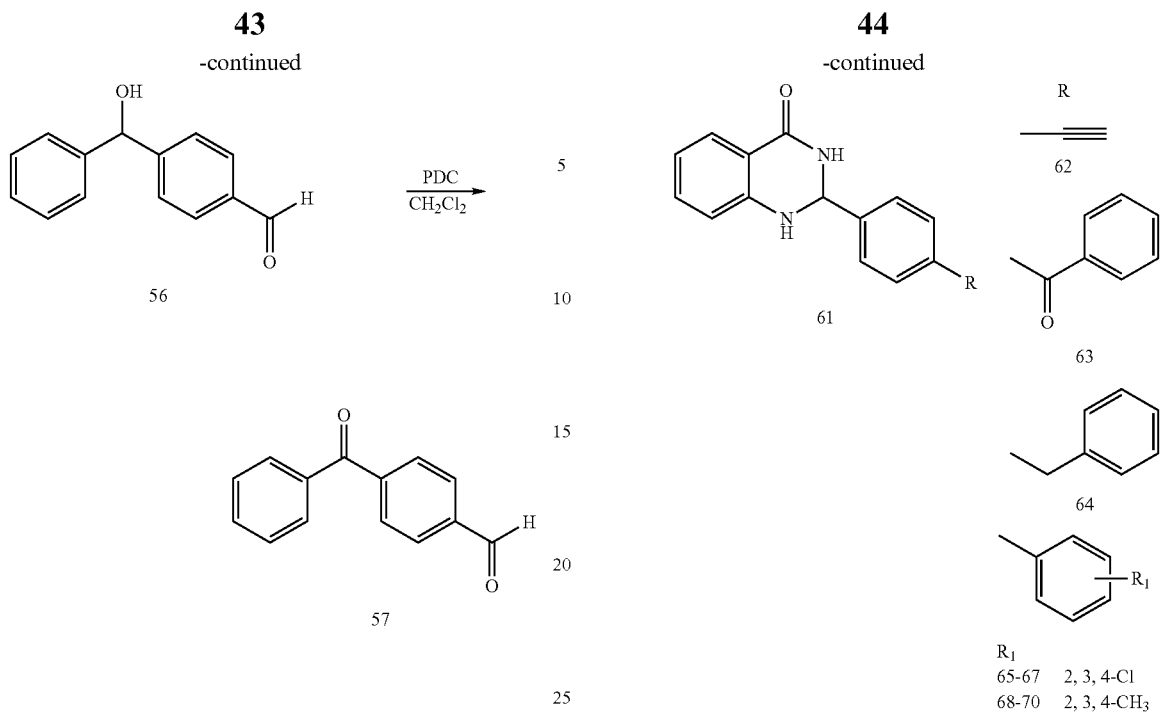

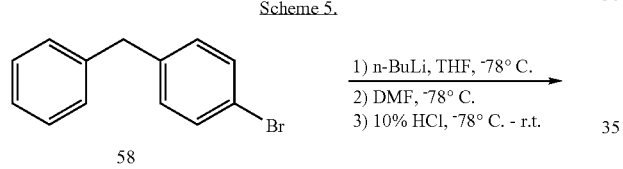

Scheme 5.

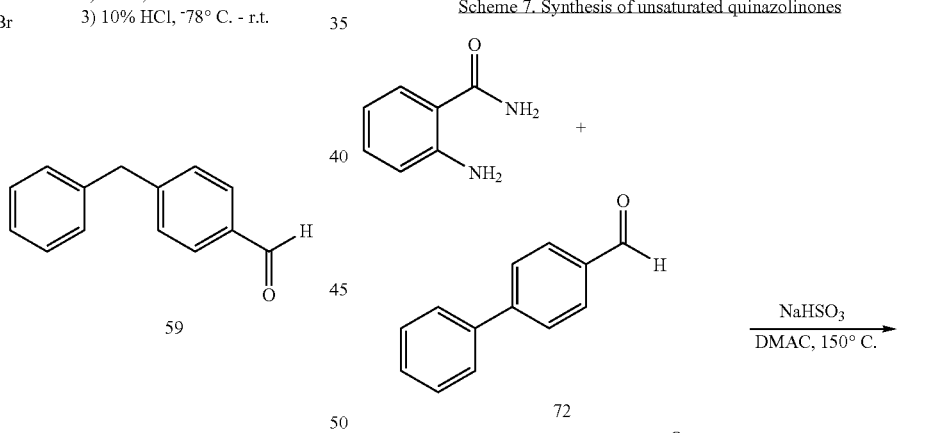

Scheme 6. Synthesis of second generation analogues 62-70.

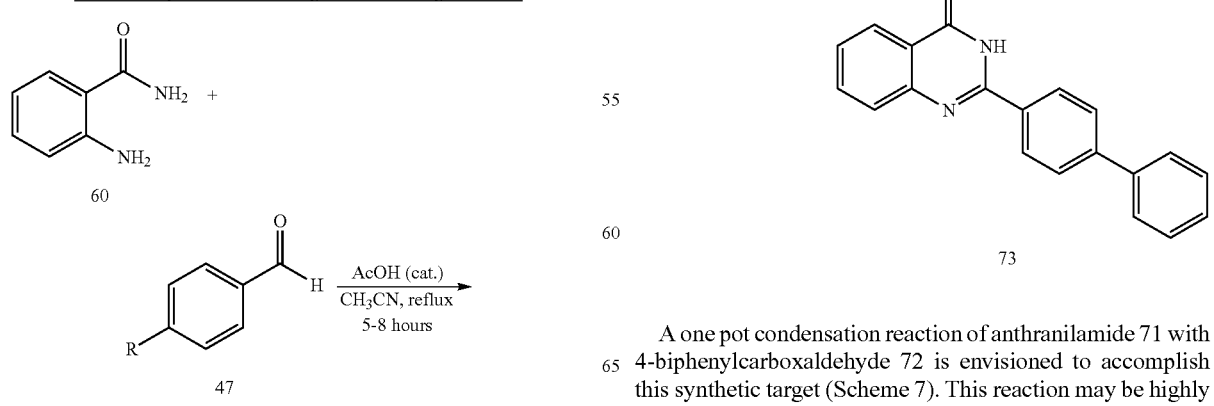

Synthesis of these analogues will be accomplished using the same procedure described for SC-2-71 (Scheme 1). It will also require the condensation of the appropriate aldehyde (as outlined in above sections).

Scheme 7. Synthesis of unsaturated quinazolinones

A one pot condensation reaction of anthranilamide 71 with 4-biphenylcarboxaldehyde 72 is envisioned to accomplish this synthetic target (Scheme 7). This reaction may be highly adaptable to derivatization.

45

Scheme 8. Synthesis of tetrafluoroquinazolinone

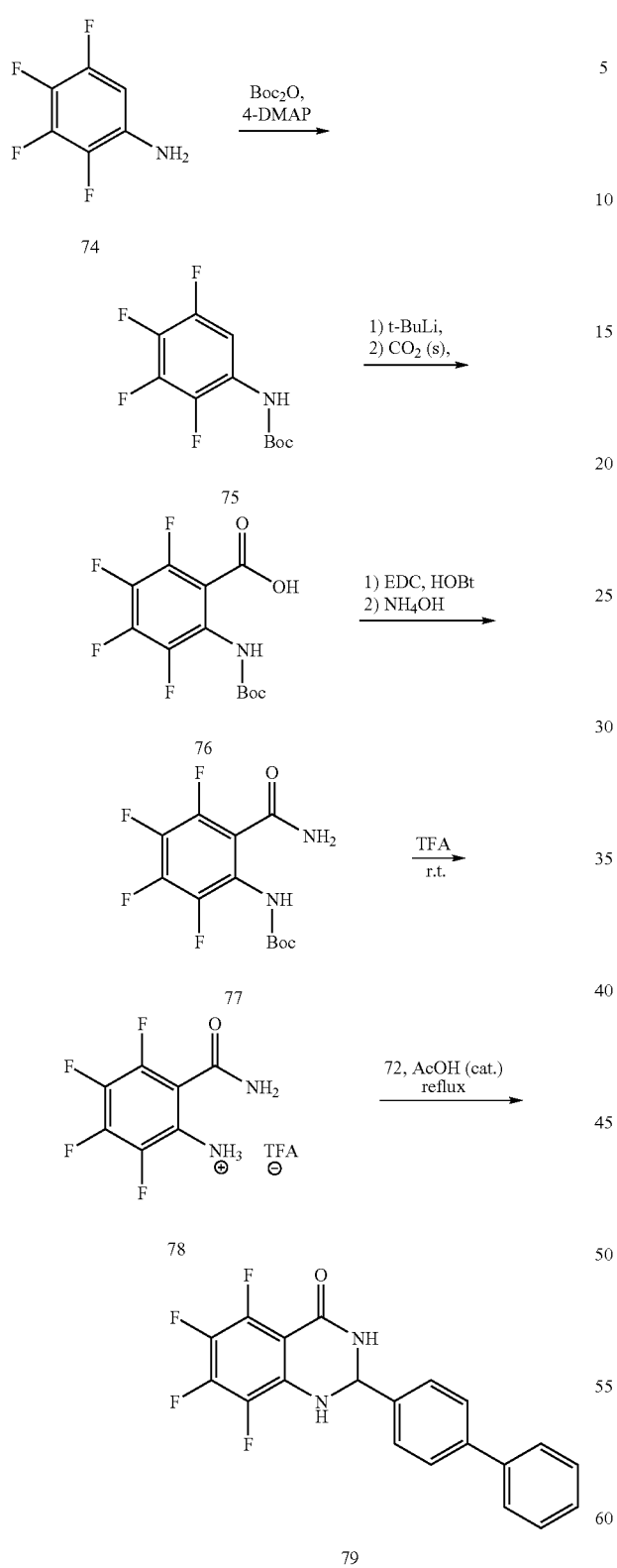

The Tetrafluoroquinazolinone 79, will be synthesized using a lateral ortholithiation of the Boc protected amine 75 (Scheme 8). Following lithiation, 76 is formed from the addition of a slurry of solid carbon dioxide in THF. This will afford the desired protected anthranilic acid derivative 76.

46

The resulting carboxylic acid will be converted to the amide 77 and condensed with 4-biphenylcarboxaldehyde to give the final compound 79.

Scheme 9. Synthesis of carbon isostere

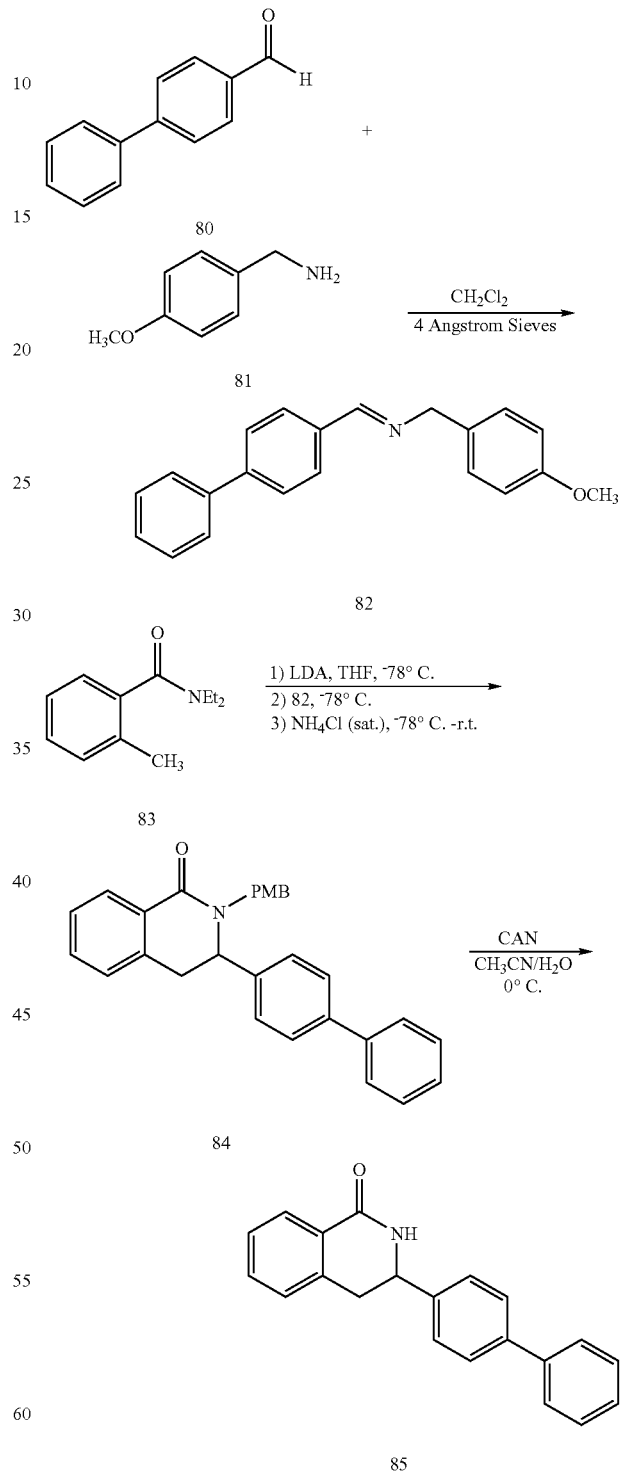

The carbon isostere of SC-2-71 will be synthesized through an imine condensation strategy (Scheme 9). This will involve forming the appropriate imine 83. Addition of 83 to the N,N-diethyl-2-methylbenzamide 83 will give the PMB protected amide 84. Deprotection with aqueous CAN (ceric ammonium nitrate) will afford the final product 85. This compound will be useful in further elucidating the importance of the amine nitrogen in our proposed NH-tyrosine 36 interaction.

Scheme 10. Synthesis of rigid analogues (amine)

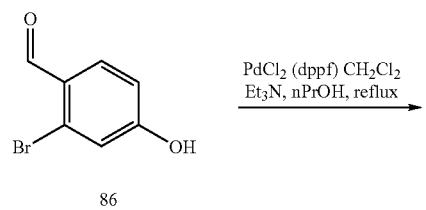

86

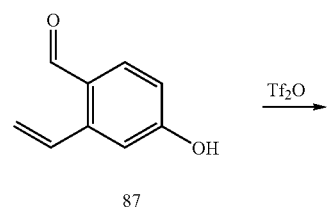

87

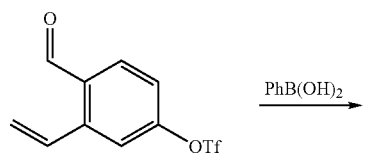

88

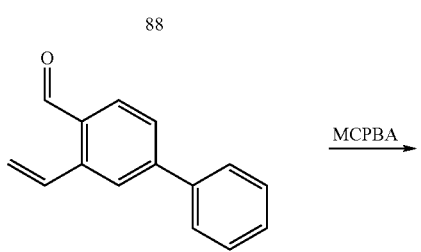

89

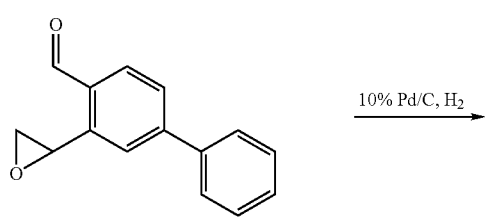

90

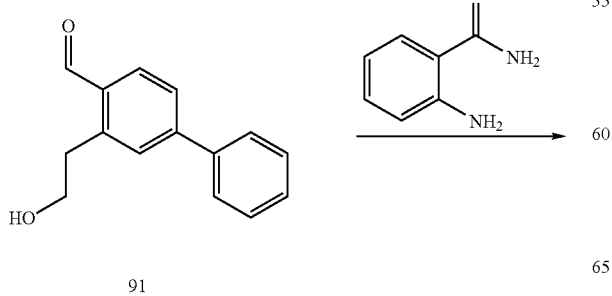

91

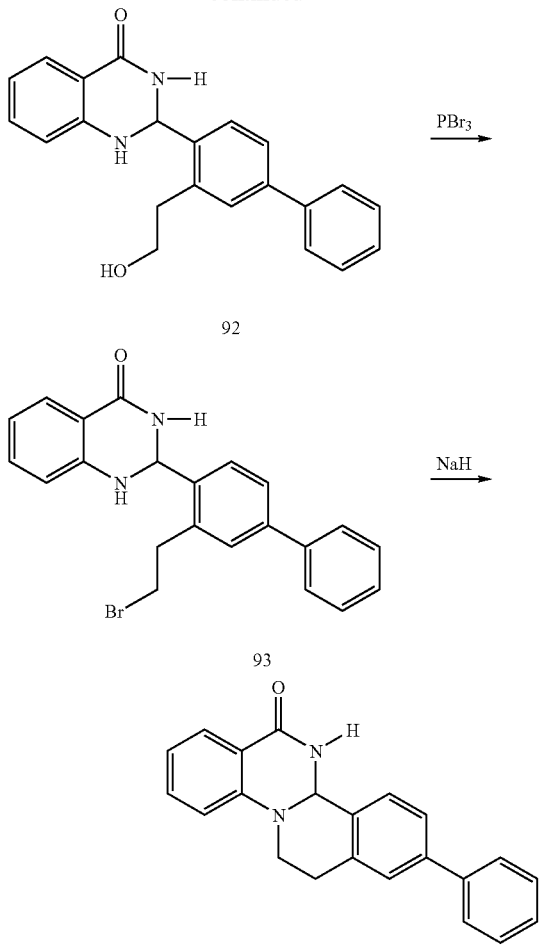

92

93

94

To synthesize rigid analogue 94 (Scheme 10), the addition of an allylic group to 86 will be accomplished by a palladium coupling reaction. The substituted phenol 87 will be triflated and then the biphenyl 89 will be preparation for a standard Suzuki coupling. Addition of MCPBA will give the epoxide 90. This will be ring opened to generate the alcohol 91. Condensation of 91 with anthranilimide will afford 92. Bromination of the alcohol with PBr3 will generate 93. Cyclization of 93 will provide the final product 94.

Scheme 11. Synthesis of rigid analogues (amide).

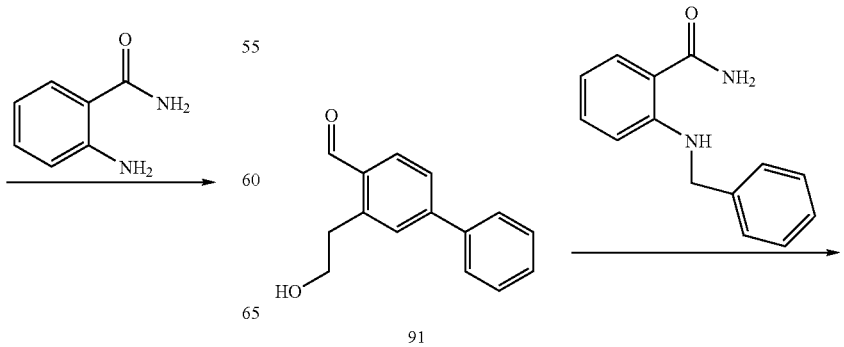

91

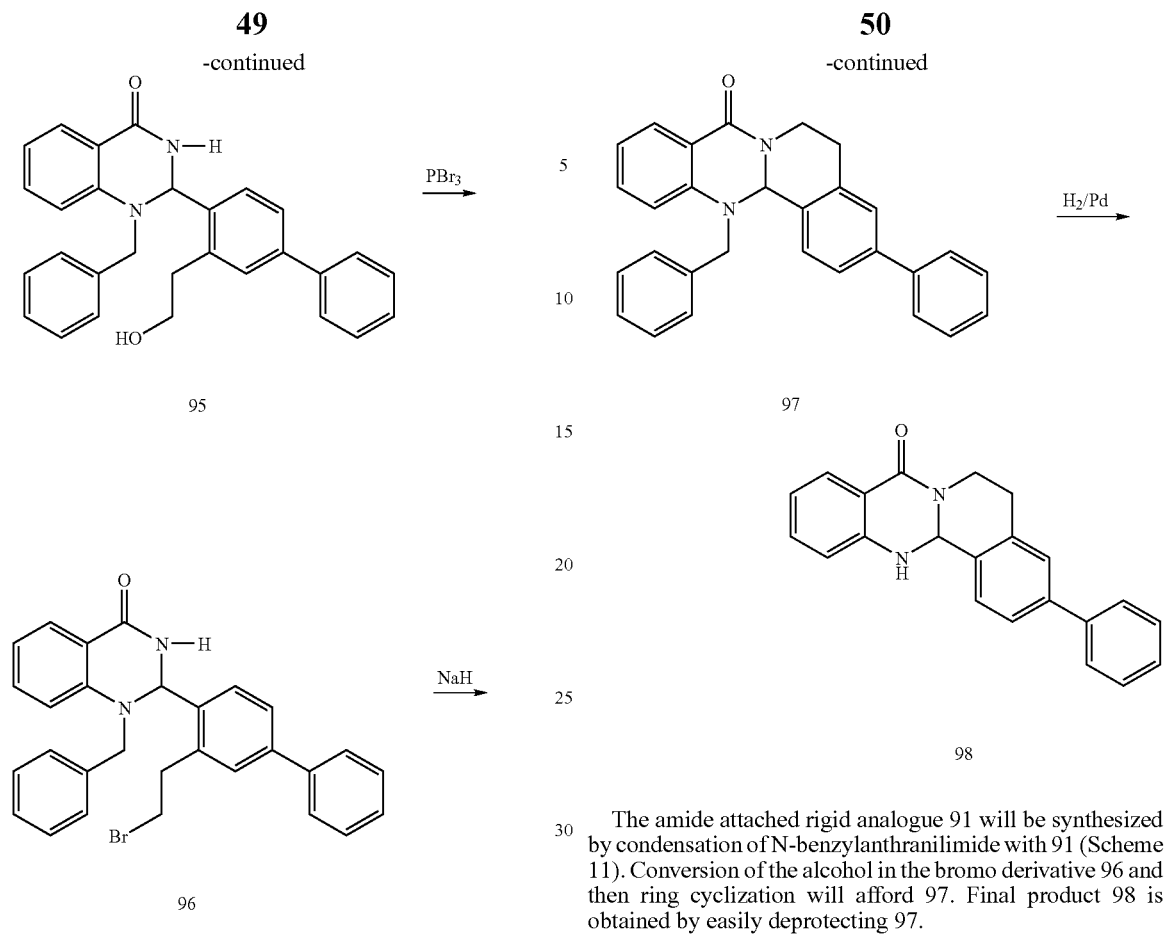
The amide attached rigid analogue 91 will be synthesized by condensation of N-benzylanthranilimide with 91 (Scheme 11). Conversion of the alcohol in the bromo derivative 96 and then ring cyclization will afford 97. Final product 98 is obtained by easily deprotecting 97.
Scheme 12.
Chiral resolution of SC-2-71.
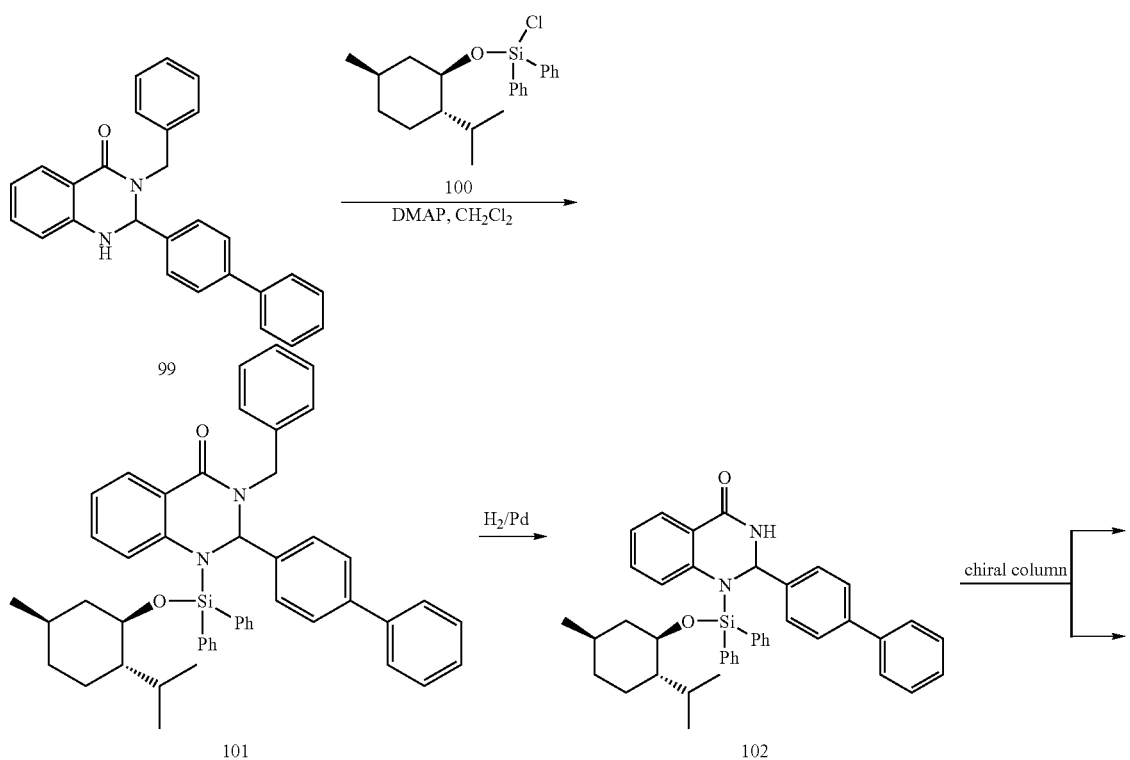

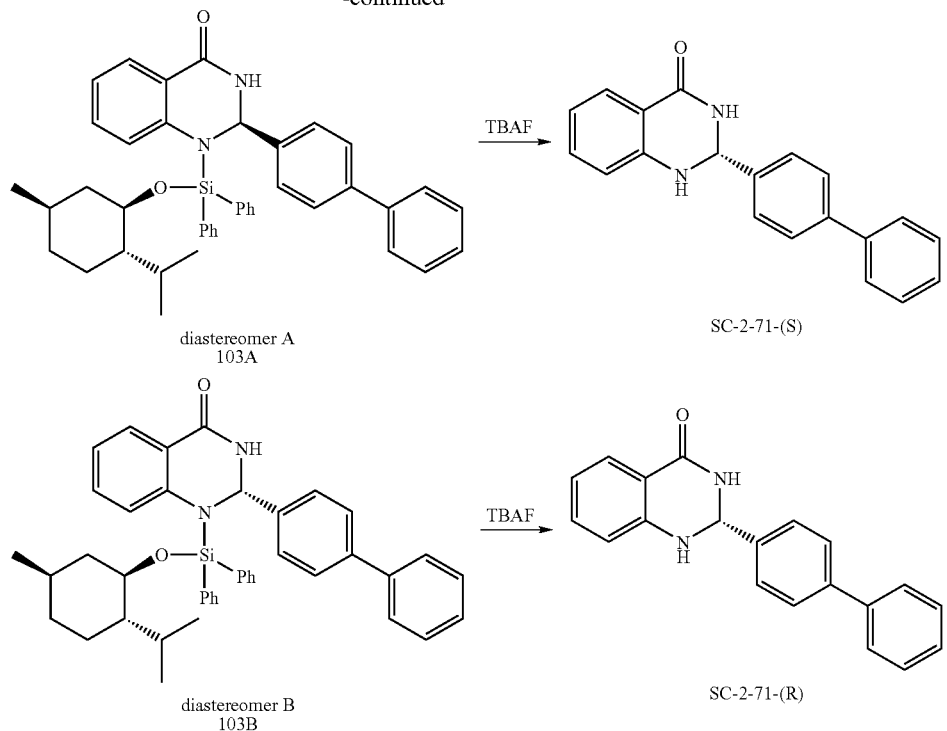

diastereomer A
103A diastereomer B
103B

SC-2-71-(S)

SC-2-71-(R)

Evaluation of enantioselective actions of SC-2-71 is important in understanding the molecular interaction with 13-tubulin and effects on cell growth. The inventor has designed a straightforward scheme to resolve the enantiomers of SC-2-71 (Scheme 12). Using benzyl protected 99, chiral siloxane 100 is added to generate 101. Deprotection of 101 and resolution of 102 on a chiral column will generate two separated diastereomers A and B. The chiral derivatizing agent will be cleaved using TBAF to afford each enantiomer (Scheme 12).

Example 7

Diagnostic Screening Assay for AMD

A significant event in the progression of AMD (age-related macular degeneration) is the rupture of the Bruch's Membrane that separates the photoreceptors from the vasculature behind the retina. When the membrane ruptures, blood vessels then grow into the retina causing damage. During angiogenesis (formation of new blood vessels) endothelial cells express $\beta_{III}$ tubulin. Normally, $\beta_{III}$ tubulin is only expressed in normal neuronal cells. Accordingly, the degree of $\beta_{III}$ tubulin expression in the retina may be an indicator of the severity of angiogenesis occurring during the development and or progression of macular degeneration, such as dry AMD.

Methods of the present invention may be used as diagnostic screen assays that may help grade the severity of macular degeneration, such as dry AMD. According to example methods, when a patient reaches a certain level of visual impairment, a physician can administer at least one compound as described herein by, for example, intravenous injection (similarly to fluorescein techniques discussed below), or intraocular injection. After a certain length of time, the compound will have reached the retina and at least some of the compound may bind to cells expressing $\beta_{III}$ tubulin. The compound can be visualized using the same or similar equipment and filters currently used for traditional angiograms and fluorescein. The excitation and emission wavelengths of certain specific compounds of the present invention may be similar enough to fluorescein that detection, for example by angiogram, is similar to well-known techniques.

Fluorescein angiography or fluorescent angiography, is a technique for examining the circulation of the retina, which involves injection of sodium fluorescein into the systemic circulation, after which an angiogram is obtained by photographing fluorescence emitted after illumination of the retina with blue light, for example at a wavelength of 490 nanometers. Such techniques may include taking baseline images prior to injecting approximately 5ml of sodium fluorescein into the vein of a patient (e.g., in the arm or hand). After the fluorescein reaches the retinal circulation (e.g., 10-12 seconds after injection), a series of photographs is taken of the retina, for example, once every second for about 20 seconds and thereafter less often. Filters, such as an excitor filter and/or a barrier filter may be used in such techniques. An excitor filter may be used to reduce the amount of non-fluorescent light that reaches the film and allow for maximum excitation of fluorescein. A barrier filter may be used to allow only yellow-green light (530 nm)(from the fluorescence) to reach the camera. Black-and-white photos may give better contrast than color photos. Color photos, although useful, are not necessary because only one color is being transmitted though the filter.

A fluorescein angiogram may be useful in, for example, revealing vascular irregularities when compared with a normal angiogram. Comparison of angiograms may be useful with respect to evaluation of diseases of the choroid, retina, and retinal vasculature. The present methods in which one or more compounds of the invention is administered to a patient, provides a more valuable tool than traditional angiograms. In particular, the present diagnostic methods provide methods for evaluating the location and/or degree $\beta_{III}$ tubulin expression, thus, allowing one to diagnose conditions in which $\beta_{III}$ tubulin expression may be a factor. Detection of the compound(s) of the present invention may indicate that $\beta_{III}$ tubulin is present. Furthermore, comparing angiograms or other detection results of the same tissue over two or more time points, using the compounds of the present invention, may be used to diagnose active changes in the levels of $\beta_{III}$, which could be indicative of angiogenic activity. In contrast, traditional compounds used to visualize retinal vasculature, such as sodium fluorescein, do not preferentially bind to $\beta_{III}$ tubulin.

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

Example 8

Staining of Endothelial Cells for βIII Tubulin

Choroidal blood vessels form as buds from vascular endothelium. In the first experiment, cultures of retinal vascular endothelial cells were stained for $\beta_{II}$ and $\beta_{III}$ Tubulin.

For $\beta_{III}$ tubulin, staining was performed on 5% buffered formalin fixed tissue (diluted in 1% PBS) to identify $\beta_{III}$-Tubulin antigens. After 10 minutes of antigen retrieval with citric acid buffer, monoclonal class $\beta_{III}$ -Tubulin antibody (1:1000, from Covance in 5% BSA) was applied drop wise, at room temperature and incubated for two hours. The slide was then rinsed with PBS for 20 minutes. PBS was decanted and Alexa Fluor 594 (1:500, from Invitrogen in PBS) secondary antibody was applied and incubated in a dark room/humidity camber for 30 minutes and then incubated for 30 minutes with PBS and coverslipped.

For $\beta_{II}$ tubulin, staining was performed on 5% buffered formalin fixed tissue (diluted in 1% PBS) to identify $\beta_{II}$-Tubulin antigens. After 10 minutes of antigen retrieval with citric acid buffer, monoclonal class $\beta_{II}$-Tubulin antibody (1:1000, from Covance in 5% BSA) was applied drop wise, at room temperature and incubated for two hours. The slide was then rinsed with PBS for 20 minutes. PBS was decanted and Alexa Fluor 488 (1:500, from Invitrogen in PBS) secondary antibody was applied and incubated in a dark room/humidity camber for 30 minutes and then incubated for 30 minutes with PBS and coverslipped. Data not shown.

Example 9

Staining of Retinal Mounts for $\beta_{III}$ Tubulin

In this experiment, choroidal tissue from patients with wet AMD and choroidal tissue from normal patients were stained for both the $\beta_{II}$ and $\beta_{III}$ isoforms of tubulin, using a double labeled immunofluorescence staining procedure. After antigen retrieval, monoclonal class $\beta_{II}$-Tubulin antibody (1:1000, from Covance in 5% BSA) was applied and visualized with Alexa Fluor 488 (1:1000, from Invitrogen in PBS) as the secondary antibody. Likewise, monoclonal $\beta_{III}$-Tubulin (1:1000, from Covance in 5% BSA) was applied and visualized with Alexa Fluor 594 (1:1000, from Invitrogen in PBS) as the secondary antibody.

The results of the retinal tissue mount staining are shown in FIG. 11.

What is claimed is:

1. A method of detecting the presence of $\beta_{III}$ tubulin in a specific tissue, said method comprising:
    a) administering a compound having the following formula (I) to a patient:

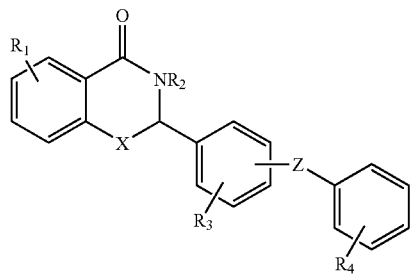

wherein $R_1$, $R_3$, and $R_4$ are independently selected from the group consisting of $NO_2$, H, halo, $C_1$-$C_4$ alkyl; $C_2$-$C_4$ alkenyl, $C_2$-$C_4$ alkynyl, $C_1$-$C_4$ alkoxy, $C_5$-$C_7$ aryl, mono-, di- or tri-chloro, and mono-, di- or tri-methyl;
   $R_2$ is H;
   X is NH; and
   Z is selected from the group consisting of a bond and CO; and
    b) waiting a predetermined length of time after said administration of said compound; and
    c) detecting said compound, wherein said detection after said predetermined length of time indicates the present of $\beta_{III}$ tubulin in said tissue;
   wherein said specific tissue is selected from the group consisting of ocular tissue, nerve tissue, mammary tissue, brain tissue, lung tissue, prostate tissue, colon tissue, and uterine tissue; and wherein said detecting comprises detecting the fluorescence of said compound using an angiogram.

2. The method of claim 1, wherein said specific tissue is retinal tissue, and detecting comprises photographing the fluorescence emitted after illumination of the retina with blue light at a wavelength of about 490 nanometers.

3. The method of claim 2, further comprising quantifying the levels of said $\beta_{III}$ tubulin in said tissue.

4. The method of claim 3, wherein the quantity of $\beta_{III}$ tubulin is a relative quantity.

5. The method of claim 3, wherein the quantity of $\beta_{III}$ tubulin is an absolute quantity.

6. The method of claim 5, wherein the tissue is the retina.

7. The method of claim 1, wherein said compound is administered via a route selected from the group consisting of topical, oral, buccal, intravenous, intramuscular, intra-arterial, intramedullary, intrathecal, intraventricular, intraocular, transdermal, subcutaneous, intraperitoneal, intranasal, enteral, sublingual, vaginal, pulmonary, and rectal.

8. The method of claim 7, wherein said compound is administered via a topical route.

9. The method of claim 8, wherein said compound is administered via a topical route using eye drops.

10. The method of claim 1, wherein the patient has or is suspected of having a disorder or condition selected from the group consisting of breast cancer, prostate cancer, ovarian cancer, melanoma, colorectal cancer, renal cancer, central nervous system cancer, leukemia, non-small cell lung cancer, rheumatoid arthritis, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, systemic lupus, polyarteritis, Wegener's sarcoidosis, scleritis, Stevens-Johnson disease, pemphigoid, radial keratotomy, corneal graph rejection, macular degeneration, sickle cell anemia, sarcoid, pseudoxanthoma elasticum, Paget's disease, vein occlusion, artery occlusion, carotid obstructive disease, chronic uveitis/vitreitis, Lyme's disease, systemic lupus erythematosus, retinopathy of prematurity, Eales' disease, Behcet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications.

11. The method of claim 10, wherein the condition is cancer and wherein said cancer is selected from the group consisting of breast cancer, prostate cancer, ovarian cancer, melanoma, colorectal cancer, renal cancer, central nervous system, leukemia, and non-small cell lung cancer.

12. The method of claim 1, wherein said patient is a human.

13. The method of claim 1, wherein;
$R_1$, $R_3$ and $R_4$ are independently selected from the group consisting of H, halo, $C_1$-$C_4$ alkyl, $C_2$-$C_4$ alkenyl, $C_2$-$C_4$ alkynyl and $C_5$-$C_6$ aryl;
X is NH;
Z is selected from the group consisting of a bond and CO; and
$R_2$ is H.

14. The method of claim 1, wherein;
$R_1$, $R_3$ and $R_4$ are independently selected from the group consisting of H, halo and $C_1$-$C_4$ alkyl;
X is NH;
Z is selected from the group consisting of a bond and CO; and
$R_2$ is H.

15. The method of claim 1, wherein said compound is

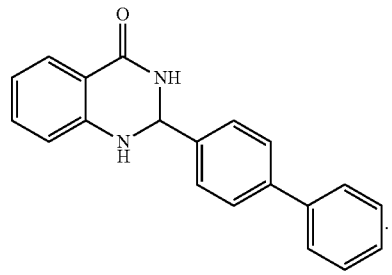

SC-2-71